(12) United States Patent
Lynn et al.

(10) Patent No.: US 8,834,918 B2
(45) Date of Patent: Sep. 16, 2014

(54) MODIFIED MULTILAYERED FILM

(75) Inventors: David M. Lynn, Middleton, WI (US); Ronald T. Raines, Madison, WI (US); Christopher M. Jewell, Madison, WI (US); Stephen M. Fuchs, Carrboro, NC (US); Ryan M. Flessner, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1167 days.

(21) Appl. No.: 12/017,953

(22) Filed: Jan. 22, 2008

(65) Prior Publication Data
US 2008/0286345 A1    Nov. 20, 2008

Related U.S. Application Data

(60) Provisional application No. 60/881,788, filed on Jan. 22, 2007.

(51) Int. Cl.
*A61L 15/16* (2006.01)
*A61K 9/70* (2006.01)
*A61K 47/48* (2006.01)

(52) U.S. Cl.
CPC ......... *A61K 9/7007* (2013.01); *A61K 47/48315* (2013.01)
USPC .......................................... 424/444; 435/375

(58) Field of Classification Search
CPC ....................... A61K 47/48315; A61K 9/7007
USPC .......................................... 424/444; 435/375
See application file for complete search history.

(56) References Cited

U.S. PATENT DOCUMENTS

| | | | |
|---|---|---|---|
| 4,304,705 A | 12/1981 | Heilmann et al. |
| 4,451,619 A | 5/1984 | Heilmann et al. |
| 4,485,236 A | 11/1984 | Rasmussen et al. |
| 4,639,286 A | 1/1987 | Rasmussen et al. |
| 4,871,824 A | 10/1989 | Heilmann et al. |
| 4,981,933 A | 1/1991 | Fazio et al. |
| 5,013,795 A | 5/1991 | Coleman et al. |
| 5,039,813 A | 8/1991 | Fazio et al. |
| 5,081,197 A | 1/1992 | Heilmann et al. |
| 5,091,489 A | 2/1992 | Heilmann et al. |
| 5,116,506 A | 5/1992 | Williamson et al. |
| 5,149,806 A | 9/1992 | Moren et al. |
| 5,262,484 A | 11/1993 | Coleman et al. |
| 5,266,446 A | 11/1993 | Chang et al. |
| 5,336,742 A | 8/1994 | Heilmann et al. |
| 5,419,806 A | 5/1995 | Huebner et al. |
| 5,486,358 A | 1/1996 | Coleman et al. |
| 5,567,422 A | 10/1996 | Greenwald |
| 5,741,620 A | 4/1998 | Holmes et al. |
| 5,837,751 A | 11/1998 | Jacobine et al. |
| 5,948,878 A | 9/1999 | Burgess et al. |
| 6,126,829 A | 10/2000 | Gunnarsson et al. |
| 6,183,644 B1 | 2/2001 | Adams et al. |
| 6,217,912 B1 | 4/2001 | Park et al. |
| 6,245,922 B1 | 6/2001 | Heilmann et al. |
| 6,274,322 B1 | 8/2001 | Curiel et al. |
| 6,291,216 B1 | 9/2001 | Muller et al. |
| 6,312,727 B1 | 11/2001 | Schacht et al. |
| 6,353,055 B1 | 3/2002 | Kabanov et al. |
| 6,365,173 B1 | 4/2002 | Domb et al. |
| 6,379,952 B1 | 4/2002 | Rasmussen et al. |
| 6,383,811 B2 | 5/2002 | Wolf et al. |
| 6,387,262 B1 | 5/2002 | Rittmann et al. |
| 6,395,253 B2 | 5/2002 | Levy et al. |
| 6,544,790 B1 | 4/2003 | Sabatini |
| 6,586,524 B2 | 7/2003 | Sagara |
| 6,645,374 B2 | 11/2003 | Cote et al. |
| 6,652,886 B2 | 11/2003 | Ahn et al. |
| 6,740,643 B2 | 5/2004 | Wolff et al. |
| 6,743,521 B2 | 6/2004 | Hubbell et al. |
| 6,770,740 B1 | 8/2004 | Rice et al. |
| 6,998,115 B2 | 2/2006 | Langer et al. |
| 7,112,361 B2 | 9/2006 | Lynn et al. |
| 7,303,677 B2 | 12/2007 | Cote et al. |
| 7,332,546 B2 | 2/2008 | Fansler et al. |
| 7,368,296 B2 | 5/2008 | Edwards et al. |
| 2001/0006817 A1 | 7/2001 | Pack et al. |
| 2001/0025015 A1 | 9/2001 | Volker et al. |
| 2001/0031839 A1 | 10/2001 | Muller et al. |
| 2002/0012652 A1 | 1/2002 | Levy et al. |

(Continued)

FOREIGN PATENT DOCUMENTS

| | | |
|---|---|---|
| WO | WO 01/76594 | 10/2001 |
| WO | WO 2004/009665 | 1/2004 |
| WO | WO 2004/009666 | 1/2004 |
| WO | WO 2008/116029 | 9/2008 |

OTHER PUBLICATIONS

Fuchs et al "Polyarginine as a multifunctional fusion tag," Protein Science (2005), 14:1538-1544.*

(Continued)

*Primary Examiner* — Suzanne Ziska
(74) *Attorney, Agent, or Firm* — Lathrop & Gage LLP

(57) ABSTRACT

A composition for delivery of a molecule into a cell is provided. The composition includes a protein transduction domain that is conjugated to the molecule which is incorporated into a multilayered film. Preferably, the protein transduction domain is a cationic protein transduction domain. More preferably, the cationic protein transduction domain is nonaarginine, and the multilayered film includes polyelectrolyte multilayers. When the composition is presented to a cell, the multilayered film dissolves or erodes in physiological media, and the molecule is delivered into the cell.

17 Claims, 7 Drawing Sheets

(56) References Cited

U.S. PATENT DOCUMENTS

| | | |
|---|---|---|
| 2002/0131951 A1 | 9/2002 | Langer et al. |
| 2002/0146459 A1 | 10/2002 | Levy et al. |
| 2002/0150951 A1 | 10/2002 | Rasmussen et al. |
| 2002/0164315 A1 | 11/2002 | Wolff et al. |
| 2003/0026840 A1 | 2/2003 | Plank et al. |
| 2003/0049435 A1 | 3/2003 | Haddad et al. |
| 2003/0073619 A1 | 4/2003 | Mahato et al. |
| 2005/0265956 A1 | 12/2005 | Liu et al. |
| 2005/0282925 A1 | 12/2005 | Schlenoff et al. |
| 2006/0051396 A1 | 3/2006 | Hamilton et al. |
| 2006/0068204 A1 | 3/2006 | Rasmussen et al. |
| 2006/0093607 A1 | 5/2006 | Gerber et al. |
| 2006/0178430 A1 | 8/2006 | Blackwell et al. |
| 2006/0251701 A1* | 11/2006 | Lynn et al. .................. 424/426 |
| 2007/0020469 A1 | 1/2007 | Wood et al. |
| 2009/0105375 A1 | 4/2009 | Lynn et al. |
| 2009/0170179 A1 | 7/2009 | Lynn et al. |
| 2010/0048736 A1 | 2/2010 | Liu et al. |

OTHER PUBLICATIONS

Abel et al., "Fluorescence Assay for the Binding of Ribonuclease A to the Ribonuclease Inhibitor Protein," *Anal. Biochem.*, 306:100-107 (2003).

Brooks et al., "Tat peptide mediated cellular delivery: back to basics," *Adv. Drug Delivery Rev.*, 57:559-577 (2005).

Fittipaldi and Giacca, "Transcellular protein transduction using the Tat protein of HIV-1", *Adv. Drug Delivery Rev.*, 57:597-608 (2005).

Fredin et al., "Surface Analysis of Erodible Multilayered Polyelectrolyte Films: Nanometer-Scale Structure and Erosion Profiles," *Langmuir*, 21:5803-5811 (2005).

Fuchs and Raines, "Pathway for Polyarginine Entry into Mammalian Cells," *Biochemistry*, 43:2438-2444 (2004).

Fuchs and Raines, "Polyarginine as a multifunctional fusion tag," *Protein Sci.*, 14:1538-1544 (2005).

Fuchs and Raines, "Internalization of cationic peptides: the road less (or more?) traveled," *Cell. Mol. Life Sci.*, 63:1819-1822 (2006).

Futaki et al., "An Abundant Source of Membrane-Permeable Peptides Having Potential as Carriers for Intracellular Protein Delivery," *J. Biol. Chem.*, 276(8):5836-58401 (2001).

Jewell et al., "Multilayered polyelectrolyte films promote the direct and localized delivery of DNA to cells," *J. Control. Release*, 106:214-223 (2005).

Jewell et al., "Multilayered Films Fabricated from an Oligoarginine-Conjugated Protein Promote Efficient Surface-Mediated Protein Transduction," *Biomacromolecules*, 8:857-863 (2007).

Haigis and Raines, "Secretory ribonucleases are internalized by a dynamin-independent endocytic pathway," *J. Cell Sci.*, 116:313-324 (2003).

Ho et al., "Synthetic Protein Transduction Domains: Enhanced Transduction Potential in Vitro and in Vivo," *Cancer Research*, 61:474-477 (2001).

Li and Haynie, "Multilayer Biomimetics: Reversible Covalent Stablization of a Nanostructured Biofilm," *Biomacromolecules*, 5:1667-1670 (2004).

Lynn, "Layers of opportunity: nanostructured polymer assemblies for the delivery of macromolecular therapeutics," *Soft Matter*, 2:269-273 (2006).

Mitchell, "Polyarginine enters cells more efficiently than other polycationic homopolymers," *J. Pept. Res.*, 56:318-325 (2000).

Nori and Kopecek, "Intracellular targeting of polymer-bound drugs for cancer chemotherapy," *Adv. Drug Delivery Rev.*, 57:609-636 (2005).

Schwarze et al., "In Vivo Protein Transduction: Delivery of a Biologically Active Protein into the Mouse," *Science*, 285:1569-1572 (1999).

Snyder and Dowdy, "Cell Penetrating Peptides in Drug Delivery," *Pharm. Res.*, 21(3):389-393 (2004).

Wadia and Dowdy, "Transmembrane delivery of protein and peptide drugs by TAT-mediated transduction in the treatment of cancer," *Adv. Drug Delivery Rev.*, 57:579-596 (2005).

Wender et al., "The design, synthesis, and evaluation of molecules that enable or enhance cellular uptake: Peptoid molecular transporters," *Proc. Natl. Acad. Sci. USA*, 97:13003-13008 (2000).

Ai et al. (Feb. 2003) "Biomedical Applications of Electrostatic Layer-by-Layer Nano-assembly of Polymers, Enzymes, and Nanoparticles," *Cell Biochem. Biophys.* 39(1):23-43.

Akinc et al. (2003) "Parallel Synthesis and Biophysical Characterization of a Degradable Polymer Library for Gene Delivery," *J. Am. Chem. Soc.* 125(18):5316-5323.

Aldersle et al. (1974) "Intramolecular Catalysis of Amide Hydrolysis by the Carboxy-Group. Rate Determining Proton Transfer from External General Acids in the Hydrolysis of Substituted Maleamic acids," *J. Chem. Soc. Perk. Trans.* 2 :1487-1495.

Anderson et al. (Apr. 30, 1998) "Human Gene Therapy," *Nature* 392(Supp):25-30.

Barrera et al. (1993) "Synthesis and RGD Peptide Modification of New Biodegradable Copolymer: Poly(Lactic Acid-co-lysine)," *J. Am. Chem. Soc.* 115(23):11010-11011.

Benns et al. (2000) "pH-Sensitive Cationic Polymer Gene Delivery Vehicle: N-Ac-poly(L-histidine)-graft-poly(L-lysine) Comb Shaped Polymer," *Bioconjugate Chem.* 11:637-645.

Berg et al. (2006) "Controlled Drug Release from Porous Polyelectrolyte Multilayers," *Biomacromolecules* 7:357-364.

Bertrand et al. (Apr. 2000) "Ultrathin Polymer Coatings by Complexation of Polyelectrolytes at Interfaces: Suitable Materials, Structure and Properties," *Macromol. Rapid Comm.* 21(7):319-348.

Bindels et al. (1985) "The Reaction of Citraconic Anhydride with Bovine α-crystallin Lysine Residues. Surface Probing and Dissociation-reassociation studies," *Biochem. Biophys. Acta.* 828:255-260.

Blacklock et al. (Jan. 2007) "Disassembly of Layer-by-Layer Films of Plasmid DNA and Reducible TAT Polypeptide," *Biomaterials* 28(1):117-124.

Boussif et al. (Aug. 1995) "A Versatile Vector for Gene and Oligonucleotide Transfer into Cells in Culture and in Vivo: Polyethylenimine," *Proc. Nat. Acad. Sci.* USA 92:7297-9301.

Boulmedais et al. (2003) "Buildup of Exponentially Growing Multilayer Polypeptide Films with Internal Secondary Structure," *Langmuir* 19(2):440-445.

Bronich et al. (Sep. 6, 2000) "Recognition of DNA Topology in Reactions Between Plasmid DNA and Cationic Copolymers," *J. Am. Chem. Soc.* 122(35):8339-8343.

Buck et al. (2007) "Layer-by-Layer Assembly of Reactive Ultrathin Films Mediated by Click-Type Reactions of Poly(2-Alkenyl Azlactone)s," *Adv. Mater.* 19(22):3951-3955.

Chan et al. (1997) "Triplex DNA: Fundamentals, Advances, and Potential Applications for Gene Therapy," *J. Mol. Med.* 75:267-282.

Chen et al. (Mar. 2001) "Fabrication of a Covalently Attached Multilayer Film via In-Situ Reaction," *Macromol. Rapid Commun.* 22:311-314.

Chen et al. (2007) "Tunable Film Degradation and Sustained Release of Plasmid DNA from Cleavable Polycation/Plasmid DNA Multilayers under Reactive Conditions," *Small* 3(4):636-643.

Cho et al. (2003) "Polymeric Multilayer Films Comprising Deconstructable Hydrogen-Bonded Stacks Confined Between Electrostatically Assembled Layers," *Macromolecules* 36(8):2845-2851.

Cotton et al. (1993) "[42] Receptor-Mediated Transport of DNA into Eukaryotic Cells," *Methods Enzymol.* 217:618-644.

Crystal, R.G. (Oct. 20, 1995) "Transfer of Genes to Humans: Early Lessons and Obstacles to Success," *Science* 270(5235):404-410.

Decher, G. (Aug. 1997) "Fuzzy Nanoassemblies: Toward Layered Polymeric Multicomposites," *Science* 277:1232-1237.

De Geest et al. (Apr. 2006) "Intracellularly Degradable Polyelectrolyte Microcapsules," *Adv. Mater.* 18(8):1005-1009.

De Geest et al. (2007) "Release Mechanisms for Polyelectrolyte Capsules," *Chem. Soc. Rev.* 36:636-649.

Dixon et al. (1968) "Reversible Blocking of Amino Groups with Citraconic Anhydride," *Biochem. J.* 109:312-314.

Doubrow, M. (1992) *Microcapsules and Nanoparticles in Medicine and Pharmacy*, CRC Press, Boca Raton, pp. 17-44.

Drtina et al. (1996) "Highly Cross-Linked Azlactone Functional Supports of Tailorable Polarity," *Macromolecules* 29(13):4486-4489.

Dubas et al. (2001) "Multiple Membranes from "True" Polyelectrolyte Multilayers," *J. Am. Chem. Soc.* 123(22):5368-5369.

(56) References Cited

OTHER PUBLICATIONS

Dubas et al. (2001) "Polyelectrlyte Multilayers Containing a Weak Polyacid: Construction and Deconstruction," *Macromolecules* 34(11):3736-3740.
Etienne et al. (2005) "Degradability of Polysaccharides Multilayer Films in the Oral Environment: An in Vitro and in Vivo Study," *Biomacromolecules* 6(2):726-733.
Feng et al. (Jul. 2006) "Fabrication of Robust Biomolecular Patters by Reactive Microcontact Printing on N-Hydroxysuccinimide Ester-Containing Polymer Films," *Adv. Funct. Mater.* 16(10):1306-1312.
Feng et al. (2005) "Reactive Thin Films as Platforms for the Immobilization of Biomolecules," *Biomacromolecules* 6(6):3243-3251.
Fishbein et al. (2005) "Site Specific Gene Delivery in the Cardiovascular System," *J. Control. Release* 109:37-48.
Fishbein et al. (2006) "Bisphosphonate-Mediated Gene Vector Delivery from the Mental Surfaces of Stents," *Proc. Natl. Acad. Sci. USA* 103:159-164.
Forrest etl al. (2003) "A Degradable Polyethylenimine Derivative with Low Toxicity for Highly Efficient Gene Delivery," *Bioconjugate Chem.* 14(5):934-940.
Fredin et al. (2005) "Surface Analysis of Erosion Multilayered Polyelectrolyte Films: Nanometer-Scale Structure and Erosion Profiles," *Langmuir* 21:5803-5811.
Fredin et al. (2007) "Nanometer-Scale Decomposition of Ultrathin Multilayered Polyelectrolyte Films," *Langmuir* 23:2273-2276.
Funhoff et al. (Jan. 2004) "Polymer Side-Chain Degradation as a Tool to Control the Destabilization of Polyplexes," *Pharm. Res.* 21(1):170-176.
Geske et al. (2007) "Modulation of Bacterial Quorum Sensing with Synthetic Ligands: Systematic Evaluation of N-Acylated Homoserine Lactones in Multiple Species and New Insights into Their Mechanisms of Action," *J. Am. Chem. Soc.* 129:13613-13625.
Godbey et al. (Apr. 1999) "Tracking the Intracellular Path of Poly(ethylenimine)/DNA Complexes for Gene Delivery," *Proc. Nat. Acad. Sci. USA* 96:5177-5181.
Godbey et al. (1999) "Size Matters: Molecular Weight Affects the Efficient of Poly(ethylenimine) as a Gene Delivery Vehicle," *J. Biomed. Mater. Res.*45:268-275.
Goeddel (1990) "Systems for Heterologous Gene Expression," *Methods Enzymol.* 185:3-7.
Gonzalez et al. (1999) "New Class of Polymers for the Delivery of Macromolecular Therapeutics," *Bioconjugate Chem.* 10:1068-1074.
Gosselin et al. (2001) "Efficient Gene Transfer Using Reversibly Cross-Linked Low Molecular Weight Poluethylenimine," *Bioconjugate Chem.* 12:989-994.
Grayson et al. (2003) "Multi-Pulse Drug Delivery from a Resorbable Polymeric Microchip Device," *Nat. Mater.* 2:767-772.
Groth et al. (2004) "Layer-by-Layer Deposition of Polyelectrolytes—A Versatile Tool for the in Vivo Repair of Blood Vessels," *Angew Chem. Int. Ed. Engl.* 43:926-928.
Guichard et al. (1998) "Reactive poly(2-vinyl-4,4-dimethyl-5-oxazolone) and poly [(2-vinyl-4,4-dimethyl-5-oxazolone)-co-(methyl methacrylate)]s. Synthesis, characterization and chemical modification with 4-methoxy-4'-(β-aminoethoxy) biphenyl," *Macromol. Chem. Phys.* 199:1657-1674.
Hammond, P.T. (2004) "From and Function in Multilayer Assembly: New Applications at the Nanoscale," *Adv. Mater.* 16:1271-1293.
Heilmann et al. (Nov. 1, 2001) "Chemistry and Technology of 2-Alkenyl Azlactones," *J. Polym. Sci. A Polym. Chem.* 39(21):3655-3677.
Hiller et al. (2002) "Reversibly Erasable Nanoporous Anti-Reflection Coatings from Polyelectrolyte Multilayers," *Nat. Mater.* 1:59-63.
Jeong et al. (2001) "DNA Transfection Using Linear Poly(ethylenimine) Prepared by Controlled Acid Hydrolysis of Poly(2-ethyl-2-oxazoline)," *J. Control. Release* 73:391-399.
Jessel et al. (Jun. 6, 2006) "Multiple and Time-Schedules in Situ DNA Delivery Mediated by β-Cyclodextrin Embedded in a Polyelectrolyte Multilayer," *Proc Nat. Acad. Sci. USA* 103(23):8618-8621.
Jewell et al. (2008) "Surface-Mediated Delivery of DNA: Cationic Polymers Take Charge," *Curr. Opin. Colloid Interface Sci.* 13:395-402.
Jewelll et al. (2008) "Multilayered Polyelectrolyte Assemblies as Platforms for the Delivery of DNA and Other Nucleic Acid-Based Therapeutics," *Adv. Drug Deliv. Rev.* 60:979-999.
Jewell et al. (2006) Release of Plasmin DNA from Intravascular Stents Coated with Ultrathin Multilayered Poly *Biomacromolecules* 7:2483-2491.
Jiang et al. (2007) "Degradable-Brushed pHEMA-pDMAEMA Synthesized ATRP and Click Chemistry for Gene Delivery," *Bioconjugate Chem.* 18(6):2077-2084.
Kirby et al. (1972) "Structure and Efficiency in Intramolecular and Enzymatic Catalysis. Catalysis of Amide Hydrolysis by the Carboxy-Group of Substituted Maleamic Acids," *J. Chem. Soc. Perk. Trans. 2* 9:1206-1214.
Kircheis et al. (2001) "Design and Gene Delivery Activity of Modified Polyethylenimines," *Adv. Drug Delivery Rev.* 53:341-358.
Klugherz et al. (2000) "Gene Delivery from a DNA Controlled-Release Stent in Porcine Coronary Arteries," *Nat. Biotechnol.* 18:1181-1184.
Kwon et al. (1989) "Pseudopoly(amino Acids): A Study of the Synthesis and Characterization of poly(trans-4-hydroxy-N-acyl-L-proline esters)," *Macromolecules* 22(8):3250-3255.
Lahann et al. (2002) Reactive Polymer Coatings: A Platform for Patterning Proteins and Mammalian Cells onto a Broad Range of Materials, *Langmuir* 18(9):3632-3638.
Lahann et al. (2003) "Reactive Polymer Coatings: A First Step Toward Surface Engineering of Microfluidic Devices," *Anal. Chem.* 75(9):2117-2122.
Lavalle et al. (2004) "Direct Evidence for Vertical Diffusion and Exchange Processes of Polyanions and Polycations in Polyelectrolyte Multilayer Films," *Macromolecules* 37(3):1159-1162.
Lee et al. (2007) "A Protein Nanocarrier from Charge-Conversion Polymer in Response to Endosomal pH," *J. Am. Chem. Soc.* 129(17):5362-5363.
Liang et al. (2004) "Multilayer Assembly and Patterning of Poly(p-phenylenecinylene)s via Covalent Coupling Reactions," *Langmuir* 20(22):9600-9606.
Liang et al. (2006) *Funct. Mater.* 16:542-548.
Lim et al. (1999) "A Self-Destroying Polycationic Polymer: Biodegradable Poly(4-hydroxy-L-proline Ester)," *J. Am. Chem. Soc.* 121(24):5633-5639.
Lim et al. (2000) "Development of a Safe Gene Delivery System Using Biodegradable Polymer, Poly[alpha-(4-aminobutyl)-L-glycolic Acid]," *J. Am. Chem. Soc.* 122:6524-6525.
Little et al. (2004) "Poly-Beta Amino Ester-Containing Microparticles Enhance the Activity of Nonviral Genetic Vaccines," *Proc. Nat. Acad. Sci. USA* 101:9534-9539.
Liu et al. (2008) "Polyelectrolyte Multilayers Fabricated from 'Charge-Shifting' Anionic Polymers: A New Approach to Controlled Film Disruption and the Release of Cationic Agents from Surfaces," *Soft Matter* 4:1688-1695.
Liu et al. (2005) "Charge-Shifting Cationic Polymers that Promote Self-Assembly and Self-Disassembly with DNA," *Macromolecules* 38:7907-7914.
Lu et al. (Feb. 2008) "Biodegradable Polycation and Plasmid ZDNA Multilayer Film for Prolonged Gene Delivery to Mouse Osteoblasts," *Biomaterials* 29(6):733-741.
Luo et al. (2000) "Synthetic DNA Delivery Systems," *Nat. Biotechnol.* 18:33-37.
Luten et al. (2006) "Methacrylamide Polymers with Hydrolysis-Sensitive Cationic Side Groups as Degradable Gene Carriers," *Bioconjugate Chem.* 17(4):1077-1084.
Lvov et al. (1994) "Assembly of Thin Films by Means of Successive Deposition of Alternate Layers of DNA and Poly(allylamine)," *Macromolecules* 26(20):5396-5399.
Lynn, D.M. (2007) "Peeling Back the Layers: Controlled Erosion and Triggered Disassembly of Multilayered Polyelectrolyte Thin Films," *Adv. Mater.* 19:4118-4130.

(56) References Cited

OTHER PUBLICATIONS

Lynn et al. (2000) "Degradable Poly(beta-amino Esters): Synthesis Characterization, and Self-Assembly with Plasmid DNA," *J. Am. Chem. Soc.* 122:10761-10768.
Lynn et al. (2001) "Accelerated Discovery of Synthetic Transfection Vectors: Parallel Synthesis and Screening of a Degradable Polymer Library," *J. Am. Chem. Soc.* 123:8155-8156.
Mathiowitz et al. (1987) "Polyanhydride Microspheres as Drug Carriers. I. Hot-Melt Microencapsulation," *J. Controlled Release* 5:13-22.
Mathiowitz et al. (1987) "Novel Microcapsules for Delivery Systems," *Reactive Polymers* 6:275-283.
Mathiowitz et al. (1988) "Polyanhydride Microspheres as Drug Carriers. II. Microencapsulation by Solvent Removal," *J. Appl. Polymer Sci.* 35:755-774.
Mattmann et al. (2008) "Synthetic Ligands that Activate and Inhibit a Quorum-Sensing Regulator in *Pseudomonas aeruginosa*," *Bioorg. Med. Chem. Lett.* 18:3072-3075.
Mendelsohn et al. (2006) "Fabrication of Microporous Thin Films from Polyelectrolyte Multilayers," *Langmuir* 16(11):5017-5023.
Meyer et al. (Sep. 2007) "A dimethylmaleic Acid-Melittin-polylysine Conjugate with Reduced Toxicity, pH-Triggered Endosomolytic Activity and Enhanced Gene Transfer Potential," *J. Gene Med.* 9(9):797-805.
Midoux et al. (1999) "Efficient Gene Transfer by Histidylated Polylysine/pDNA Complexes," *Bioconjugate Chem.* 10:406-411.
Nolte et al. (2004) "Creating Effective Refractive Index Gradients Within Polyelectrolyte Multilayer Films: Molecularly Assembled Rugate Filters," *Langmuir* 20(8):3304-3310.
Oupicky et al. (2002) "Laterally Stabilized Complexes of DNA with Linear Reducible Polycations: Strategy for Triggered Intracellular Activation of DNA Delivery Vectors," *J. Am. Chem. Soc.* 124(1):8-9.
Pack et al. (2005) "Design and Development of Polymers for Gene Delivery," *Nat. Rev. Drug Disc.* 4:581-593.
Perlstein et al. (2003) "DNA Delivery from an Intravascular Stent with a Denatures Collagen-Polylactic-Polyglycolic Acid-Controlled Release Coating: Mechanisms of Enhanced Transfection," *Gene Ther.* 10:1420-1428.
Peterson et al. (2002) "Poly(ethyleneimine-co-L-lactamide-co-succinamide): A Biodegradable Polyethyleneimine Derivative with an Advantageous pH-Dependant Hydrolytic Degradation for Gene Delivery," *Bioconjugate Chem.* 13:812-821.
Peyratout et al. (Jul. 19, 2004) "Tailor-Made Polyelectrolyte Microcapsules: From Multilayers to Smart Containers," *Angew. Chem. Int. Ed.* 43(29):3762-3783.
Picart et al. (Oct. 1, 2002) "Molecular Basis for the Explanation of the Exponential Growth of Polyelectrolyte Multilayers," *Proc. Nat. Acad. Sci. USA* 99(20):12531-12535.
Picart et al. (Nov. 2005) "Controlled Degradability of PolySaccharide Multilayer Films in Vitro and in Vivo," *Adv. Funct. Mater.* 15(11):1771-1780.
Pichon et al. (2002) "Poly[Lys-(AEDTP)]: A Cationic Polymer that Allows Dissociation of pDNA/Cationic Polymer Complexes in a Reductive Medium and Enhances Polyfection," *Bioconjugate Chem.* 13:76-82.
Prata et al. (2004) "Charge-Reversal Amphiphiles for Gene Delivery," *J. Am. Chem. Soc.* 126(39):12196-12197.
Putnam et al. (1999) "Poly(4-hydroxy-1-proline Ester): Low-Temperature Polycondensation and Plasmid DNA Complexation," *Macromolecules* 32:3658-3662.
Putnam et al. (Jan. 30, 2001) "Polymer-Based Gene Delivery with Low Cytotoxicity by a Unique Balance of Side-Chain Termini," *Proc. Nat. Acad. Sci USA* 98(3):1200-1205.
Ren et al. (Mar. 2006) "Construction and Enzymatic Degradation of Multilayered Poly-l-lysine/DNA Films," *Biomaterials* 27(7):1152-1159.
Ren et al. (2006) "Tunable DNA Release from Cross-Linked Ultrathin DNA/PLL Multilayered Films," *Bioconjugate Chem.* 17(1):77-83.

Richardson et al. (2001) "Polymeric System for Dual Growth Factor Delivery," *Nat. Biotechnol.* 19:1029-1034.
Richert et al. (2004) "Improvement of Stability and Cell Adhesion Properties of Polyelectrolyte Multilayer Films by Chemical Cross-Linking," *Biomacromolecules* 5(2):284-294.
Richert et al. (2004) "Layer by Layer Buildup of Polysaccharide Films: Physical Chemistry and Cellular Adhesion Aspects," *Langmuir* 20(2):448-458.
Rozema et al. (2003) "Endosomolysis by Masking of a Membrane-Active Agent (EMMA) for Cytoplasmic Release of Macromolecules," *Bioconjugate Chem.* 14(1):51-57.
Rozema et al. (Aug. 7, 2007) "Dynamic PolyConjugates for Targeted in Vivo Delivery of siRNA to Hepatocytes," *Proc. Nat. Acad. Sci. USA* 104(32):12982-12987.
Saltzman et al. (Mar. 2002) "Building Drug Delivery into Tissue Engineering Design," *Nat. Rev. Drug Discov.* 1(3):177-186.
Santini et al. (Jan. 29, 1999) "A Controlled-Release Microchip," *Nature* 397:335-338.
Saul et al. (Nov. 2007) "Delivery of Non-Viral Carriers from Sphere-Tem plated Fibrin Scaffolds for Sustained Transgene Expression," *Biomaterials* 28(31):4705-4716.
Schneider et al. (2007) "Multifunctional Polyelectrolyte Multilayer Films: Combining Mechanical Resistance, Biodegradability, and Bioactivity," *Biomacromolecules* 8(1):139-145.
Schneider et al. (2006) "Polyelectrolyte Multilayers with a Tunable Young's Modulus: Influence of Film Stiffness on Cell Adhesion," *Langmuir* 22(3):1193-1200.
Schoeler et al. (2003) "Growth of Multilayer Films of Fixed and Variable Charge Density Polyelectrolytes: Effect of Mutual Charge and Secondary Interactions," *Macromolecules* 36(14):5258-5264.
Schuler et al. (2001) "Decomposable Hollow Biopolymer-Based Capsules," *Biomacromolecules* 2:921-926.
Segura et al. (2002) "Surface-Tethered DNA Complexes for Enhanced Gene Delivery," *Bioconjugate Chem.* 13(3):621-629.
Shea et al. (1999) "DNA Delivery from Polymer Matrices for Tissue Engineering," *Nat. Biotechnol.* 17:551-554.
Serizawa et al. (2003) "Time-Controlled Desorption of Ultrathin Polymer Films Triggered by Enzymatic Degradation," *Angew Chem. Int. Ed.* 42(10):1115-1118.
Serizawa et al. (2002) "Thermoresponsive Ultrathin Hydrogels Prepared by Sequential Chemical Reactions," *Macromolecules* 35(6):2184-2189.
Shetty et al. (1980) "Ready Separation of Proteins from Nucleoprotein Complexes by reversible Modification of Lysine Residues," *Biochem. J.* 191:269-272.
Shim et al. (2008) "Controlled Delivery of Plasmid DNA and siRNA to Intracellular Targets Using Ketalized Polyethylenimine," *Biomacromolecules* 9(2):444-455.
Such et al. (2006) "Assembly of Ultrathin Polymer Multilayer Films by Click Chemistry," *J. Am. Chem. Soc.* 128(29):9318-9319.
Suh et al. (Apr. 1, 2003) "Efficient Active Transport of Gene Nanocarriers to the Cell Nucleus," *Proc. Nat. Acad. Sci. USA* 100(7):3878-3882.
Sukhishvili et al. (2002) "Layered, Erasable Polymer Multilayers Formed by Hydrogen-Bonded Sequential Self-Assembly," *Macromolecules* 35(1):301-310.
Sukhishvili et al. (2000) "Layered, Erasable, Ultrathin Polymer Films," *J. Am. Chem. Soc.* 122(39):9550-9551.
Sukhishvili, S.A. (2005) "Responsive Polymer Films and Capsules via Layer-by-Layer Assembly," *Curr. Opin. Colloid. Interface Sci.* 10:37-44.
Sun et al. (2007) "Assembly of Multilayers Films Using Well-Defined, End-Labeled Poly (acrylic Acid): Influence of Molecular Weight on Exponential Growth in a synthetic Weak Polyelectrolyte System," *Langmuir* 23(16):8452-5459.
Sun et al. (2000) "Covalently Attached Multilayer Assemblies by Sequential Adsorption of Polycationic Diazo-Resins and Polyanionic Poly(acrylic acid)," *Langmuir* 16(10):4620-4624.
Takahashi et al. (2003) "Transgene Delivery of Plasmid DNA to Smooth Muscle Cells and Macrophages from a Biostable Polymer-Coated Stent," *Gene Ther.* 10:1471-1478.

(56) References Cited

OTHER PUBLICATIONS

Takashi et al. (2007) "Delivery of Large Biopharmaceuticals from Cardiovascular Stents: An Alternative Strategy for Inhibition of Restenosis," *Biomacromolecules* 8(11):3281-3293.
Tang et al. (2006) "Biomedical Applications of Layer-by-Layer Assembly: From Biomimetics to Tissue Engineering," *Adv. Mater.* 18(24):3203-3224.
Thomas et al. Nov. 12, 2002) "Enhancing Polyethylenimine's Delivery of Plasmid DNA into Mammalian Cells," *Proc. Nat. Acad. Sci. USA* 99(23):14640-14645.
Vazquez et al. (Nov. 27, 2002) "Construction of Hydrolytically-Degradable Thin Films Via Layer-by-Layer Deposition of Degradable Polyelectrolytes," *J. Am. Chem. Soc.* 124(47):13992-13993.
Verma et al. (Sep. 18, 1997) "Gene Therapy—Promises, Problems and Prospects," *Nature* 389:239-242.
Veron et al. (2004) "New Hydrolyzable pH-Responsive Cationic Polymers for Gene Delivery: A Preliminary Study," *Macromol. Biosci.* 4(4):431-444.
Walter et al. (2004) "Local Gene Transfer of phVEGF-2 Plasmid by Gene-Eluting Stents: An Alternative Strategy for Inhibition of Restenosis," *Circulation* 110:36-45.
Wang et al. (2001) "A Novel Biodegradable Gene Carrier Based on Polyphosphoester," *J. Am. Chem. Soc.* 123:9480-9481.
Wolff et al. (Dec. 2001) "Nuclear Security Breached," *Nat. Biotechnol.* 19:1118-1120.
Wolff, J.A. (Aug. 2002) "The 'Grand' Problem of Synthetic Delivery," *Nat. Biotechnol.* 20:768-769.
Wood et al. (2005) "Tunable Drug Release from Hydrolytically Degradable Layer-by-Layer Thin Films," *Langmuir* 21:1603-1609.
Wood et al. (2006) "Controlling Interlayer Diffusion to Achieve Sustained, Multi-Agent Delivery from Layer-by-Layer Films," *Proc. Nat. Acad. Sci. USA* 103:10207-10212.
Wu et al. (Oct. 1, 2002) "Cell-Biological Applications of Transfected-Cell Microarrays," *Trends Cell Biol.* 12(10):485-488.
Xie et al. (Jan. 5, 1999) "Design of Reactive Porous Polymer Supports for High Throughput Bioreactors: Poly(2-vinyl-4,4-dimethylazlactone-co-acrylamide-co-ethylene dimethacrylate) Monoliths," *Biotechnol. Bioeng.* 62(1):30-35.
Xu et al. (Jun. 25, 2007) "Targeted Charge-Reversal Nanoparticles for Nuclear Drug Delivery," *Angew Chem. Int. Ed.* 46(26):4999-5002.
Yang et al. (2004) "Mechanistic Study of the Anchoring Behavior of Liquid Crystals Supported on Metal Salts and Their Orientational Responses to Dimethyl Methylphosphonate," *J. Phys. Chem. B* 108(52):20180-20186.
Yang et al. (2002) "Micropatterning of Polymer Thin Films with pH-Sensitive and Cross Linkable Hydrogen-Bonded Polyelectrolyte Multilayers," *J. Am. Chem. Soc.* 124(10):2100-2101.
Yin et al. (1998) "Architectural Copolymers: Rod-Shaped, Cylindrical Dendrimers," *J. Am. Chem. Soc.* 120:2678-2679.
Zelikin et al. (2006) "Disulfide Cross-Linked Polymer Capsules: En Route to Biodeconstructible Systems," *Biomacromolecules* 7(1):27-30.
Zelikin et al. (2003) "Competitive Reactions in Solutions of Poly-L-histidine, Calf Thymus DNA, and Synthetic Polyanions: Determining the Binding Constants of Polyelectrolytes," *J. Am. Chem. Soc.* 125:13693-13699.
Zhang et al. (2002) "Ways for fabricating stable layer-by-layer self assemblies: combined ionic self-assembly and post chemical reaction," *Colloid Surface A* 198:439-442.
Zhang et al. (2003) "Fabrication of Stable Hollow Capsules by Covalent Layer-by-Layer Self-Assembly," *Macromolecules* 36(11):4238-4240.
Zhang et al. (2006) "Structure/Property Relationships in Erodible Multilayered Films: Influence of Polycation Structure on Erosion Profiles and the Release of Anionic Polyelectrolytes," *Langmuir* 22:239-245.
Zhang et al. (2007) "Ultrathin Multilayered Films Assembled from 'Charge-Shifting' Cationic Polymers: Extended, Long-Term Release of Plasmid DNA from Surfaces," *Adv. Mater.* 19:4218-4223.
Zhang et al. (2007) "Multilayered Films Fabricated from Plasmid DNA and a Side-Chain Functionalized Poly(Beta-amino ester): Surface-Type Erosion and Sequential Release of Multiple Plasmid Constructs from Surfaces," *Langmuir* 23:11139-11146.
Zhang et al. (2006) Multilayered Films Fabricated from Combinations of Degradable Polyamines: Tunable Erosion and Release of Anionic Polyelectrolytes, Macromolecules 39:8928-8935.
Zhang et al. (2006) "Erosion of Multilayered Assemblies Fabricated from Degradable Polyamines: Characterization and Evidence in Support of a Mechanism that Involves Polymer Hydrolysis," *J. Poly. Sci. A Poly. Chem.* 44:5161-5173.
Zhang et al. (2004) "Multilayered Thin Films that Sustain the Release of Functional DNA under Physiological Conditions," *Langmuir* 20(19):8015-8021.
Zhou et al. (1990) "Preparation of Poly9L-serine ester): A Structural Analog of Conventional Poly(L-serine)," *Macromolecules* 23(14):3399-3406.
Ziauddin et al. (May 3, 2001) "Microarrays of Cells Expressing Defined cDNAs," *Nature* 411:107-110.

* cited by examiner

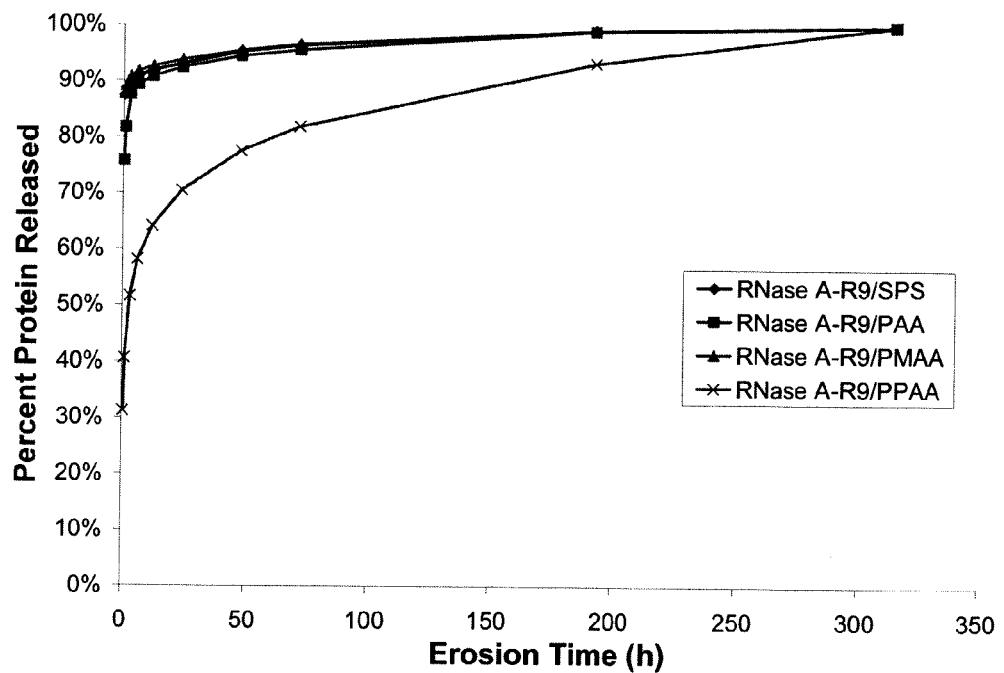

MODIFIED MULTILAYERED FILM

CROSS-REFERENCE TO RELATED APPLICATIONS

This invention claims priority to U.S. Provisional Patent Application Ser. No. 60/881,788, filed Jan. 22, 2007.

GOVERNMENT INTERESTS

This invention was made with United States government support awarded by the National Institutes of Health, NIH grants EB002746, CA073808, and GM044783. The United States government has certain rights in the invention.

FIELD OF THE INVENTION

This invention is related to the field of delivery of molecules into cells.

BACKGROUND OF THE INVENTION

The alternating, layer-by-layer adsorption of positively and negatively charged polymers on surfaces is a convenient and versatile method for the fabrication of well-defined, nanostructured thin films. The stepwise nature of this process permits precise control over the compositions, thicknesses, and surface properties of multilayered assemblies fabricated from a wide variety of water-soluble polymers. The ability to incorporate biologically-active species such as peptides, proteins, and DNA into these assemblies without loss of biological function has made possible the development of catalytically- and biologically-active thin films, membranes, and microcapsules with potential applications in many areas of biology, biotechnology, and medicine (Lynn, 2006, *Soft Matter* 2: 269-273).

Past work describing the incorporation of proteins into multilayered polyelectrolyte assemblies has focused largely on naturally occurring (that is, wild-type) proteins. Manipulating the pH or ionic strength of polyelectrolyte, protein, or polypeptide solutions used during fabrication, can influence the growth and structures of these films as well as the structure and function of incorporated proteins. One general limitation of this approach, however, is that assembly conditions and film properties are often dependent upon the magnitude and sign of the net charge, isoelectric point, and other physical properties of the native proteins or polyelectrolytes that are used. Model peptides rationally designed to contain high densities of cationic residues (e.g., lysine) or anionic residues (e.g., glutamic acid) can be used to facilitate the assembly of multilayered films using layer-by-layer procedures (Li and Haynie, 2004, *Biomacromolecules* 5: 1667-1670).

BRIEF SUMMARY

This invention provides compositions for delivery of small molecules into cells. The small molecules delivered into cells may be various molecules, including but not limited to nucleic acids, drugs, toxins, carbohydrates, metabolites, peptides, proteins, or other molecules. The compositions include charged small molecule transduction domains that are conjugated to the molecules and incorporated into multilayered films. The multilayered films are capable of dissolving in physiological media.

The charged small molecule transduction domains may be cationic protein transduction domains. These domains may include cationic oligoaminoacid tails with lengths of between 2 and about 30 residues. The cationic protein transduction domains may include polyarginine. The polyarginine may be nonaarginine. The compositions of this invention may further include one or more linkers conjugated to the charged small molecule transduction domains.

The multilayered films may include polyelectrolyte multilayers. The multilayered films may include one or more anionic polymers. In one embodiment, the anionic polymer may be sodium polystyrene sulfonate [poly(styrene sulfonate)]. In other embodiments, the anionic polymer may be selected from the group consisting of sodium poly(styrene sulfonate), poly(acrylic) acid, poly(methacrylic) acid, and poly($\alpha$-propylacrylic acid).

In some embodiments, the molecules that are delivered into cells are preferably a peptide or a protein. In some embodiments, the protein delivered into cells may be RNase A.

The compositions of the present invention may include at least one layer that is free of charged small molecule transduction domain-conjugated molecule. In some embodiments, the compositions may include films that comprise eight layers of polymer alternating with eight layers of the charged small molecule transduction domain-conjugated molecule.

This invention provides methods for fabrication of multilayered assemblies. The methods include: providing a substrate; depositing at least one layer free of charged small molecule transduction domain on the substrate; and depositing at least one layer comprising charged small molecule transduction domain conjugated to a molecule on the substrate, wherein the layers are capable of dissolving in physiological media. In the methods, the charged small molecule transduction domain may be a cationic protein transduction domain.

This invention provides methods, which include contacting the compositions of the present invention with cells for times that are sufficient to allow the conjugated molecules to enter the cells.

The present invention provides methods for delivery of small molecules into cells. The methods include: a) providing a composition comprising a charged small molecule transduction domain conjugated to a molecule, and a multilayered film comprising two or more layers, wherein the multilayered film is capable of dissolving in physiological media, wherein the charged small molecule transduction domain-conjugated molecule is incorporated into at least one layer of the multilayered film; and b) contacting the composition with the cell for a time sufficient to allow the small molecule to enter the cell. In the methods, the charged small molecule transduction domain may be a cationic protein transduction domain. The cationic protein transduction domains may include polyarginine. The polyarginine may be nonaarginine. In some embodiments of the methods, at least one layer in the multilayered film comprises an anionic polymer. In some examples, the anionic polymer may be selected from the group consisting of sodium poly(styrene sulfonate), poly(acrylic) acid, poly(methacrylic) acid, and poly($\alpha$-propylacrylic acid).

BRIEF DESCRIPTION OF THE DRAWINGS

FIG. 7 is a plot illustrating the percent of protein released over time for eight bilayer RNase A-R9/SPS, RNase A-R9/PAA, RNase A-R9/PMAA, RNase A-R9/PPAA films incubated in PBS buffer at 37° C.

DETAILED DESCRIPTION OF THE DRAWINGS AND THE PRESENTLY PREFERRED EMBODIMENTS

Figure 1:
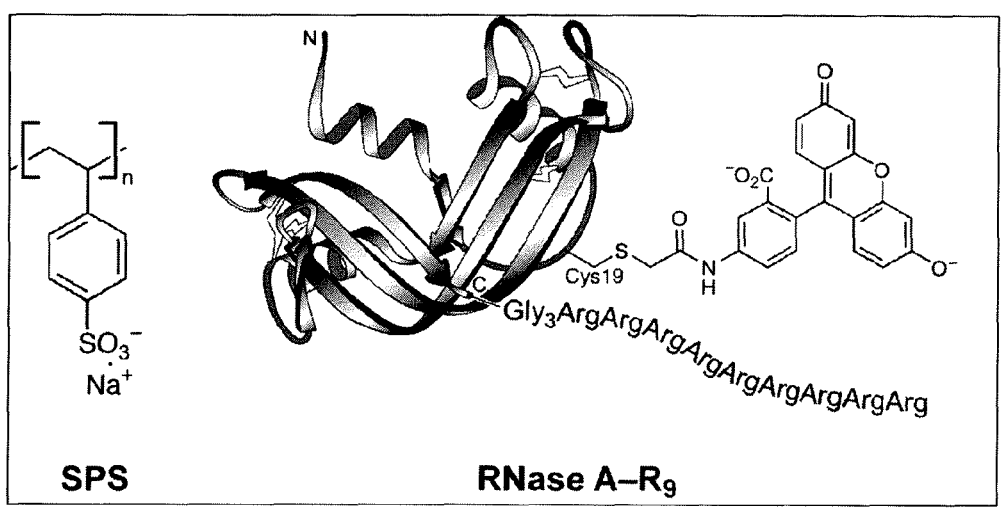
FIG. 1 is a schematic illustration of the structures of sodium polystyrene sulfonate (SPS) and fluorescein-labeled RNase A-$R_9$ used in this invention (N=amino terminus, C=carboxyl terminus, Cys=cysteine, Gly=glycine, Arg=arginine).

For the purpose of promoting an understanding of the principles of the invention, reference will now be made to certain preferred embodiments thereof and specific language will be used to describe the same. It will nevertheless be understood that no limitation of the scope of the invention is thereby intended. Any alterations, further modifications and applications of the principles of the invention as described herein are being contemplated as would normally occur to one skilled in the art to which the invention relates.

Unless defined otherwise, all technical and scientific terms used herein have the same meaning as commonly understood to one of ordinary skill in the art to which this invention belongs. In order to provide a clear and consistent understanding of the specification and the claims, the following definitions are provided.

The terms "a", "an", "the" and the like, unless otherwise indicated, include plural forms.

"Multilayered film" refers to a film fabricated by depositing or adsorbing in a stepwise manner more than one layer of material. As understood by one of skill in the art, this term is also synonymous with "polyelectrolyte multilayer (PEM)". As would also be understood by one of skill in the art, these terms are used generally to describe films fabricated in the manner described above, and are not intended to imply anything specific about the internal structures or organization of the films.

"Nonamer" refers to a molecule with nine residues. For example, "nonaarginine" refers to nine residues of arginine (R$_9$ or R9); "nonalysine" refers to nine residues of lysine (K$_9$ or K9).

"Small molecule transduction domain" refers to a domain that can cross biological membranes efficiently independent of transporters or specific receptors and promote the delivery of molecules into cells. As used herein, "molecules" include, but are not limited to, nucleic acids, drugs, toxins, carbohydrates, metabolites, peptides, proteins, or other molecules. The small molecule transduction domain may be charged, i.e., it may carry a net charge. The small molecule transduction domain may be a charged oligomeric sequence. A "cationic small molecule transduction domain" is a small molecule transduction domain that includes cationic residues and carries a net cationic charge. As used herein, a small molecule transduction domain may be natural or non-natural domain that, when appended to or conjugated to a molecule, promotes the internalization of the molecule by cells.

"Protein transduction domain" (PTD) refers generally to oligomeric or polymeric species that can cross biological membranes efficiently independent of transporters or specific receptors and promote the delivery of molecules such as peptides or proteins into cells. A "cationic protein transduction domain" is a PTD that includes cationic residues and carries a net cationic charge. For example, the HIV Tat ("transactivator") protein may act as a protein transduction domain. "PTD" is used herein to describe natural or non-natural sequences that, when appended to or conjugated to a small molecule such as a peptide or a protein, promote the internalization of the peptide or the protein by cells.

"Delivery" of a molecule into a cell refers to the process through which a molecule is made available to and subsequently internalized by a cell. For example, when a molecule is presented to a cell using the compositions and method of the present invention, the molecule is delivered into the cell.

"Physiological media" refers to media that surrounds a cell, and for the purposes of this invention refers to cells both in vivo and in vitro. Physiological media may be media in which a cell is bathed.

This invention provides compositions that can be used for delivery of molecules into cells. The compositions include surfaces that can be designed to deliver materials into biological systems. Preferably, these surfaces are thin films, e.g. thin plastic films or variations thereof. More preferably, these compositions are polyelectrolyte multilayers (PEMs). In one preferred example, the surfaces include a multilayered film. For practicing this invention, these surfaces or multilayered films are easily dissolved upon contact with physiological media. Dissolving also refers to eroding, disrupting, or falling apart of the film.

This invention provides for the conjugation of a protein transduction domain to a molecule that one desires to deliver to, or insert into, a cell. Such molecules that are delivered to, or inserted into, cells, may, e.g., be proteins that are designed to perform desired biochemical or biological functions.

In one embodiment, the protein transduction domain is a cationic protein transduction domain. Appending short, cationic peptides or non-natural, cationic oligomers to proteins can facilitate their uptake by cells. For example, the conjugation of nonaarginine (R$_9$) to fluorescently-labeled RNase A (FIG. 1) dramatically increases the cellular internalization of RNase A without loss of ribonucleolytic activity. For the purposes of this invention, the minimum length of a cationic peptide is two peptide residues. Various cationic PTDs can be used for practicing this invention, e.g. oligomers using arginine, lysine, combinations of arginine and lysine, or other natural or synthetic sequences composed of other charged groups.

The cationic PTDs of the present invention can include a different number of residues. The minimal number of resides is two. For example when the cationic transduction domain includes arginine residues, the minimal number of arginine residues is two. In some embodiments, the number of arginine residues is between two and about thirty. Preferably, the number of arginine residues is nine (i.e., nonaarginine, R$_9$ or R9). In addition to the biological activity endowed by cationic protein transduction domains, the conjugation of PTDs such as R$_9$ to molecules such as proteins also provides a general and straightforward method for conferring cationic charge without compromising protein function. For example, conjugation of R$_9$ to RNase A increases its adsorption onto negatively-charged glass and silica substrates (Fuchs and Raines, 2005, *Protein Sci.* 14: 1538-1544). More than one protein transduction domain can be conjugated with a molecule that is to be delivered to, or inserted into, a cell.

Preferably, the molecules that are delivered into cells are biomolecules, including peptides, proteins, nucleic acids, drugs, toxins, carbohydrates, metabolites, or other small molecules that are suitable for delivery into, or insertion into, a cell. The molecules can also be modified, mutagenized, or engineered with different properties.

One aspect this invention combines the incorporation of conjugated molecules into multilayered films and the use of protein transduction domains to deliver conjugated molecules into a cell. The surface-localized release of the conjugated molecules promotes efficient internalization of the molecules by cells.

In one aspect, the methods of this invention provide a general approach to facilitate incorporation of proteins into multilayered polyelectrolyte assemblies using anionic polyelectrolytes. The cationic protein transduction domain conjugated molecule is incorporated into the layers of film. Such a composition that includes a multilayered assembly is presented to the desired cell or cells. Once the multilayered film is dissolved or eroded, the molecule is delivered into, or inserted into, the cell or cells.

The composition of this invention may further include a molecular linker conjugated to the protein transduction domain. For example, the linker can be directly attached to the cationic oligopeptide. Such molecular linkers could be used to conjugate other molecules for import into cells, including non-proteinaceous molecules, carbohydrates, secondary metabolites, drugs, toxic molecules, etc.

This invention provides for the fabrication of multilayered assemblies that can be used for delivery of molecules into cells. Preferably, the multilayered assemblies can be 10-1000 nm thick. More preferably, the multilayered assemblies are about 80 nm thick. The multilayered assemblies may include different numbers of layers. In some embodiments, the number of layers in the multilayered assemblies may range from 2 layers to about 200 layers. Preferably, the number of layers in the multilayered assemblies is between 2 layers and 50 layers, and more preferably the number of layers in the multilayered assemblies is between 5 layers and 15 layers. In one example, the desired film thickness may be proportional to the desired concentration of the protein or molecule that is being delivered to the tissues or the cells.

The multilayered assemblies are preferably protein-containing assemblies that make use of a cationic protein transduction domain conjugated to a functional protein. Such assemblies permit the efficient and spatially-localized delivery of functional proteins to cells and could prove useful for the localized release of therapeutic proteins from the surfaces of objects coated with multilayered polyelectrolyte assemblies.

In one embodiment, the compositions of the present invention contemplate the use of different combinations of layers of different polymers. For example, the multilayered polyelectrolyte assemblies may include one or more bottom layers that are comprised of slow-release material, and one or more top layers that are comprised of fast-release material, to provide different (e.g., two-stage) kinetics of release. In the multilayered assemblies, it is possible to use combinations of layers that include more than one type of polymer, and it is also possible to include more than one type of protein or molecule for delivery (e.g., more than one type of protein, drug, nucleic acid, or other desired molecule).

Multilayered polyelectrolyte assemblies can be disrupted, dissolved, or eroded in a variety of ways, e.g. upon changes in environmental pH, ionic strength, or other factors that change the nature of physical interactions in ionically-crosslinked materials. Thus, macroscopic objects coated with these materials can be used to mediate high levels of protein transduction in mammalian cells. In some embodiments, the present invention provides methods for delivery of a molecule into a cell, comprising contacting a composition of this invention with the cell, where the modified multilayered film is dissolved or eroded, and where the molecule is delivered into the cell.

In one preferred embodiment, the multilayered assemblies are fabricated using sodium polystyrene sulfonate (SPS) and bovine pancreatic ribonuclease (RNase A) conjugated to the cationic protein transduction domain nonaarginine ($R_9$) using an entirely aqueous layer-by-layer process. The conjugation of $R_9$ to RNase A permits the assembly of multilayered films under conditions that do not allow for the incorporation of the unmodified protein. Not intending to be bound by the following explanation or mechanism, $R_9$ may function as a cationic anchor and may serve to increase the strength of electrostatic interactions with SPS and facilitate layer-by-layer assembly. The RNase A-$R_9$/SPS films dissolve or erode rapidly in physiologically relevant media.

In one example, this invention provides for methods that use conjugation of nonaarginine ($R_9$) to RNase A to facilitate the incorporation of RNase A into multilayered assemblies. Subsequently, films fabricated using RNase A-$R_9$ conjugates can be used to localize the delivery of RNase A to cells. For example, it is possible to fabricate multilayered films using RNase A-$R_9$ conjugates and a model anionic polymer [sodium polystyrene sulfonate, (SPS)]. In one example of the invention, $R_9$ functions as a cationic anchor that permits the incorporation of RNase A into films under conditions that do not allow for the incorporation of unmodified RNase A. Macroscopic objects coated with these ultrathin assemblies can be used to provide spatial control over the delivery of RNase A-$R_9$ to mammalian cells. Thus, the methods of this invention could be used to develop new tools and methods for the localized, surface-mediated, spatially and temporally controlled delivery of therapeutic proteins to cells.

The compositions and methods of the present invention can be used for coating medical devices to introduce into cells and/or tissues drugs, therapeutics, or other desired molecules. The compositions and methods may be used in coating disposables such as needles, pipettes, pipette tips, tubes, petri dishes, and other labware, and generally in areas related to localized protein delivery and drug delivery, health care and development of localized therapies, and other adjacent areas of biotechnology.

There are various advantages of this invention. First, appending a cationic protein transduction domain to a functional protein facilitates film growth (i.e., incorporation of protein into multilayered films) under conditions for which native, wild-type protein cannot be used. This invention thus demonstrates and points generally toward development of new tools for the incorporation of proteins into thin films using layer-by-layer assembly techniques. Second, these films erode in physiological media, and the addition of a protein transduction domain to the protein makes it possible to spatially and/or temporally mediate localized release of protein and promote the efficient uptake of protein from the surfaces of coated objects.

In certain embodiments of the present invention, a variety of polyanions may be used as negatively charged components or layers in the films. Thus, different (longer or shorter) release times may be obtained by varying the structure of the polyanionic species. For example, polyanions useful for practicing the present invention may be either synthetic or natural, degradable or nondegradable, homopolymers or copolymers, functionalized or non-functionalized, etc., or various combinations of the above polyanions and/or other polyanions. Differences in the nature of the interactions of these polymers with a protein functionalized with a PTD or cationic oligomer can lead to differences in film growth, stability, and the release of protein. A non-limiting list of exemplary polyanions useful for practicing the present invention includes: poly (acrylic acid), poly(methacrylic acid), poly(ethylacrylic acid), poly(propylacrylic acid), hyaluronic acid, poly(L-aspartic acid), poly(L-glutamic acid), dextran sulfate, heparin, carboxymethylcellulose, alginate, carrageenan, poly(styrene sulfonate), cellulose sulfate, poly(methylene-co-guanidine), poly(vinylsulfate), DNA, RNA, or chemically functionalized derivatives of these materials. Changes to the structure of the PTDs or charged oligomers (e.g., different charges, different length, etc.) can result in a change in the nature of the interactions of the functionalized protein and oppositely charged polyelectrolytes. In general, shortening the number of charges can weaken interactions and result in less stable films that release more readily. Conversely, lengthening the tag (and thus increasing the number of charges) can strengthen interactions and result in more stable films that erode and release more slowly.

The present invention contemplates the use of oligomers that behave as protein transduction domains, where the oligomers have differing numbers of residues. With respect to the range of lengths (i.e., number of residues), it should be apparent to one of skill in the art that it would depend on the properties of the protein (i.e., its size and charge) as well as the structure of the polyanion. In some embodiments, the present invention provides for the use of protein transduction domains ranging from 2 to 30 residues, preferably between 5 and 15, and more preferably between 7 and 12 residues.

Appending a negatively charged (net anionic) oligomeric sequence, and adjusting the length, number of charges, etc., can provide for practicing the present invention using cationic polymers. In some examples, negatively charged oligomeric sequences can be useful in making the film and controlling film stability and protein release.

Non-limiting examples of different types and structures of PTDs and related types of natural or synthetic protein transduction domains that can be used for practicing the present invention, are described in the following references, which are incorporated herein by reference: Fuchs and Raines, 2005, *Protein Sci.* 14: 1538-1544; Fuchs and Raines, 2006, *Cell. Mol. Life. Sci.* 63: 1819-1822; Schwarze et al., 1999, *Science* 285: 1569-1572; Mitchell, 2000, *J. Pept Res.* 56: 318-325; Futaki et al., 2002, *J. Biol. Chem.* 276: 5836-5840; Snyder and Dowdy, 2004, *Pharm. Res.* 21: 389-393; Brooks et al., 2005, *Adv. Drug Delivery Rev.* 57: 559-577; Fittipaldi and Giacca, 2005, *Adv. Drug Delivery Rev.* 57: 597-608; Nori and Kopecek, 2005, *Adv. Drug Delivery Rev.* 57: 609-636; Wadia and Dowdy, 2005, *Adv. Drug Delivery Rev.* 57: 579-596; Fuchs and Raines, 2004, *Biochemistry* 43: 2438-2444; Ho et al., 2001, *Cancer Research* 61: 474-477; Wender et al., 2000, *Proc. Natl. Acad. Sci. USA* 97:13003-13008.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

Materials

Test grade n-type silicon wafers were obtained from Si-Tech (Topsfield, Mass.). Quartz microscope slides were purchased from Chemglass (Vineland, N.J.). Linear poly(ethylene imine) (LPEI, MW=25,000) was obtained from Polysciences (Warrington, Pa.). Poly(sodium 4-styrenesulfonate) (SPS, MW=70,000) was obtained from Aldrich (Milwaukee, Wis.). All commercial polyelectrolytes were used as received without further purification.

Hoechst 34580 and wheat germ agglutinin-Alexa 594 fluorescent stains were purchased from Invitrogen (Carlsbad, Calif.). Deionized water (18 MΩ) was used for washing steps and to prepare all polymer and protein solutions. PBS buffer was prepared by diluting commercially available concentrate (EM Science, Gibbstown, N.J.). Glass inset dishes used for laser scanning confocal microscopy (LSCM) were purchased from MatTek (Ashland, Mass.).

Poly(acrylic acid) (PAA, MW ~90,000), poly(methacrylic acid) (PMAA, MW ~100,000), and poly(α-propylacrylic acid) (PPAA, MW=4200) were obtained from Polysciences (Warrington, Pa.).

General Considerations

All buffers and polymer solutions were filtered through a 0.2 μm membrane syringe filter prior to use. Quartz and silicon substrates (3.5×0.5 cm) were cleaned with acetone, ethanol, methanol, and deionized water, dried under a stream of filtered air, and cleaned further by etching in an oxygen plasma (Plasma Etch, Carson City, Nev.) for 5 min prior to film deposition. UV/vis absorbance values used to quantify film deposition on quartz substrates were recorded using a DU 520 UV/vis Spectrophotometer (Beckman Coulter, Fullerton, Calif.) at a wavelength of 226 nm (corresponding to the absorbance maximum of SPS) in at least four different locations on each sample. The optical thicknesses of films deposited on silicon substrates were determined in at least five locations using a Gaertner LSE Stokes Ellipsometer (632.8 nm, incident angle=70°). Data were processed using the Gaertner Ellipsometer Measurement Program software package. Relative thicknesses were calculated by assuming an average refractive index of 1.58 for the multilayered films.

Fluorescence measurements of solutions used to erode multilayered films were made using a Fluoromax-3 fluorimeter (Jobin Yvon, Edison, N.J.) at an excitation wavelength of 490 nm. The mean fluorescence emission intensity was determined from intensity values recorded from 514-520 nm. Laser scanning confocal microscopy was performed using a Bio-Rad Radiance 2100 MP Rainbow Laser Scanning Confocal Microscope equipped with a multiphoton laser. Images were processed using the Bio-Rad LaserSharp 2000 Processing Kit and Adobe Photoshop 8.0.

Production and Purification of Fluorescent RNase A and RNase A-R9 Conjugates

Fluorescein-labeled RNase A and fluorescein-labeled RNase A conjugated to $R_9$ were prepared as described previously (Fuchs and Raines, 2005). Untagged variants of RNase A were produced in *Escherichia coli* and purified as described previously (Haigis and Raines, 2003, *J. Cell Sci.* 116: 313-324). Variants of RNase A containing a C— terminal $R_9$ tag were prepared by growing BL21(DE3)PlysS cells containing plasmid encoding the RNase A variant at 37° C. with shaking (250 rpm) in Terrific Broth containing ampicillin (200 µg/mL) and chloramphenicol (35 µg/mL) to an optical density of 1.6 at 600 nm.

cDNA expression was induced by adding isopropyl β-D-thiogalactopyranoside (IPTG; 1 mM). Cells were grown for an additional 4 h before harvesting. Cell pellets were resuspended in a lysis buffer of 10 mM Tris-HCl (pH 8.0) containing ethylenediaminetetraacetic acid (EDTA; 1.0 mM), NaCl (0.10 M), and phenylmethylsulfonyl fluoride (1.0 mM), and lysed by sonication. Inclusion bodies were isolated by centrifugation at 11,000×g for 45 min and solubilized in a denaturing solution of 20 mM Tris-HCl buffer (pH 8.0) containing guanidine hydrochloride (7.0 M) and EDTA (10 mM) for 4 h at room temperature. Solubilized inclusion bodies were diluted ten-fold with acetic acid (20 mM) and clarified by centrifugation. The supernatant was dialyzed overnight against the same buffer. The resulting protein was then folded overnight at 4° C. in a redox buffer of 0.1 M Tris-HCl (pH 8.0) containing EDTA (10 mM), L-arginine (0.5 M), reduced glutathione (1 mM), and oxidized glutathione (0.2 mM). Refolded protein was purified by cation-exchange chromatography on a 5 mL column of HiTrap SP-sepharose FF resin (Amersham Biosciences, Piscataway, N.J.) in 50 mM sodium acetate buffer (pH 5.0) with a linear gradient (50+50 mL) of NaCl (0-1.5 M). The identity of each variant was verified by MALDI-TOF mass spectrometry.

Ribonucleases were labeled with fluorescein at one specific residue in a surface loop by using variants in which Ala19 was replaced with a cysteine residue (Haigis and Raines, 2003). Film stability and release experiments relied on the fluorescence of the dianionic form of fluorescein. The second $pK_a$ of fluorescein is 6.3, which is much less than the pH of PBS and is likely to be even lower in the proximity of a highly cationic protein such as RNase A.

A19C RNase A or A19C RNase A-$R_9$ (100 µM) were incubated in PBS containing a 20-fold molar excess of 5-iodoacetamidofluorescein (Molecular Probes, Eugene, Oreg.) and a 3-fold molar excess of tris[2-carboxyethylphosphine] hydrochloride (TCEP) for 4 h at room temperature. The resulting solution was dialyzed overnight against 50 mM sodium acetate buffer (pH 5.0), and then purified by cation-exchange chromatography using a 5 mL HiTrap CM-Sepharose Fast Flow column with a linear gradient (50+50 mL) of NaCl (0-1.00 M for A19C RNase A; 0-2.00 M for A19C RNase A-$R_9$). Conjugation to the fluorophore was confirmed by MALDI-TOF mass spectrometry.

Preparation of Protein and Polyelectrolyte Solutions

Solutions of protein (7.0 µM with respect to concentration of RNase A) contained either fluorescein-labeled RNase A (RNase A) or fluorescein-labeled RNase A conjugated to nonaarginine (RNase A-$R_9$) and were prepared by diluting a concentrated stock with water. The concentrations of protein in stock solutions were determined by using $\epsilon=9860$ $M^{-1}$ $cm^{-1}$ for RNase A at 277 nm and correcting for the absorbance of the fluorescein moiety with the equation (Abel et al., 2003, *Anal. Biochem.* 306:100-107):

$$A_{277\,nm}^{protein} = A_{277\,nm}^{observed} - (A_{494\,nm}^{observed}/5)$$

Solutions of LPEI and SPS used for the fabrication of LPEI/SPS precursor layers (20 mM with respect to the molecular weight of the polymer repeat unit) were prepared using a 50 mM NaCl solution in water. LPEI solutions contained 5 mM HCl to aid polymer solubility. SPS solutions used for the deposition of protein/SPS layers (20 mM with respect to the polymer repeat unit) were prepared in water and the pH was adjusted to 5.0 with HCl.

PAA, PMAA, and PPAA solutions used for the deposition of protein/(PAA, PMAA, or PPAA) layers (1 mg/mL) were prepared in water while heating at 60° C.

Fabrication of Multilayered Films

All protein/SPS films were deposited on quartz or silicon substrates precoated with 10 bilayers of linear poly(ethylene imine) and polystyrene sulfonate fabricated using a previously optimized procedure (Jewell et al., 2005, *J. Control. Release* 106: 214-223; Fredin et al., 2005, *Langmuir* 21: 5803-5811). These precursor layers were deposited manually or by using an automated dipping robot (Riegler & Kirstein GmbH, Potsdam, Germany).

Multilayered films fabricated using RNase A and SPS were fabricated on these foundation layers manually using the following general protocol: (1) Substrates were submerged in a solution of protein (RNase A or RNase A-$R_9$) for 5 min; (2) substrates were removed and immersed in a wash bath of deionized water for 1 min followed by a second wash bath for 1 min; (3) substrates were submerged in a solution of SPS for 5 min; and (4) substrates were rinsed in the manner described above. This cycle was repeated until the desired number of protein and SPS layers (typically eight each) had been deposited. To produce substrates coated with multilayered films on only one side, commercially available rubber cement was applied to one face of the substrate and allowed to dry prior to dipping. Removal of the rubber cement by peeling after film fabrication yielded substrates coated with protein/SPS films on a single side.

Fabrication of Multilayered Films Using Poly(Acrylic Acid) and Poly(Acrylic Acid) Derivatives All protein/(PAA, PMAA, or PPAA) films were deposited on quartz or silicon substrates precoated with 10 bilayers of linear poly(ethylene imine) and poly(styrene sulfonate) fabricated using a previously optimized procedure (Jewell et al., 2005, *J. Control. Release* 106: 214-223; Fredin et al., 2005, *Langmuir* 21: 5803-5811). These precursor layers were deposited manually or by using an automated dipping robot (Riegler & Kirstein GmbH, Potsdam, Germany).

Multilayered films fabricated using RNase A and PAA, PMAA, or PPAA were fabricated on these foundation layers manually using the following general protocol: (1) substrates were submerged in a solution of protein (RNase A-R9) for 5 min, (2) substrates were removed and immersed in a wash bath of deionized water for 1 min followed by a second wash bath for 1 min, (3) substrates were submerged in a solution of PAA, PMAA, or PPAA heated at 60° C. for 5 min, and (4) substrates were rinsed in the manner described above. This cycle was repeated until the desired number of protein and PAA, PMAA, or PPAA layers (typically eight each) had been deposited.

Characterization of Film Stability and Protein Release Experiments

Experiments designed to evaluate film stability and characterize the release of protein from multilayered films were performed in the following general manner: film-coated substrates were placed in a plastic UV-transparent cuvette, and phosphate-buffered saline (PBS, pH 7.4, 137 mM NaCl) was added in an amount sufficient to cover the substrate. The samples were incubated at 37° C. and removed at predetermined intervals for analysis by ellipsometry (for silicon substrates) or UV/visible spectrophotometry (for quartz substrates).

Optical thickness and absorbance measurements were made in at least four different predetermined locations on each substrate. For experiments designed to monitor the concentrations of protein released into the buffer solution, fluorescence readings at 514-520 nm (corresponding to the maximum fluorescence emission range of fluorescein) were made directly on the buffer solution. After each measurement, substrates were placed in a fresh aliquot of PBS and returned to the incubator at 37° C. Measurement of the pH of the buffer at each time point indicated that pH did not change during the course of these experiments. Arbitrary fluorescence units arising from these experiments were converted to micrograms of protein released using a standard curve prepared using known concentrations of RNase A-$R_9$.

In Vitro Protein Transduction Experiments

COS-7 cells were grown in glass inset confocal microscopy dishes at initial seeding densities of $7.5 \times 10^4$ cells/mL in 3.0 mL of growth medium [90% (v/v) Dulbecco's modified Eagle's medium, 10% (v/v) fetal bovine serum, 100 units/mL penicillin, 100 µg/mL streptomycin]. Cells were allowed to grow overnight to approximately 90% confluence, and growth medium was replaced with 3.0 mL of serum-free culture medium (OptiMEM). Quartz slides coated with multilayered films on one or both sides were placed manually into dishes on top of cells. In experiments involving slides coated on a single face, the substrate was placed such that the film-coated face was in direct contact with the cells. In both cases, cells were incubated for 3 hr at 37° C. and analyzed directly (without removal of the quartz slide) using a Bio-Rad Radiance 2100 MP Rainbow LSCM. Immediately prior to imaging, cells were stained using wheat germ agglutinin (WGA)-Alexa 594 membrane stain and Hoechst nuclear stain according to the manufacturer's protocols. LSCM images were acquired using a 60×/1.40 NA oil-immersion objective. Images were recorded for populations of cells growing either directly under the film-coated substrates or in random remote locations of the culture well up to 2 mm away from the film-coated substrates. Fluorescein, Hoechst, and WGA-Alexa 594 probes were excited sequentially using laser lines at 488, 543, and 800 nm (multiphoton laser), respectively. Fluorescence emission signals were collected for three individual channels using direct scanning mode (N=1, scan speed=50 lps) and merged to create three-color images.

Proteins can be incorporated into ultrathin, multilayered polyelectrolyte assemblies using layer-by-layer fabrication procedures. Conjugation of nonaarginine ($R_9$) to RNase A (FIG. 1) leads to an increased affinity of this enzyme for glass and silica substrates. In one example of the present invention, the inventors discovered that the conjugation of nine additional cationic arginine groups to RNase A (1) increases the strength of electrostatic interactions between RNase A and negatively charged polyelectrolytes, and (2) provides a mechanism for the incorporation of RNase A into films under conditions that do not allow for incorporation of the unmodified protein (Jewell et al., 2007, *Biomacromolecules* 8: 857-863).

In addition, conjugation of short cationic peptide sequences such as $R_9$ to proteins increases their uptake by cells (Fuchs and Raines, 2005, *Protein Sci.* 14:1538-1544; Fuchs and Raines, 2006, *Cell. Mol. Life. Sci.* 63: 1819-1822). Therefore, macroscopic objects coated with films fabricated using RNase A-$R_9$ can be used to localize the delivery of RNase A to mammalian cells.

Fabrication of Films Using RNase A, RNase A-$R_9$, and Sodium Polystyrene Sulfonate Multilayered films were fabricated on planar quartz and silicon substrates to facilitate characterization of film growth and thickness by UV/vis absorbance and ellipsometry, respectively. For all experiments, substrates were precoated with a thin multilayered film composed of LPEI and SPS (approximately 30 nm thick, with a topmost layer of SPS) to provide a charged surface suitable for subsequent adsorption of RNase A or RNase A-$R_9$. In all experiments, RNase A and RNase A-$R_9$ conjugates were labeled with fluorescein at residue 19 to facilitate the visualization and tracking of RNase A in subsequent cellular internalization studies described below (see also Fuchs and Raines, 2005).

Fabrication of multilayered films was performed using an alternate dipping procedure. The iterative dipping of quartz substrates into RNase A-$R_9$ (7.0 µM in water; pH=5.0) and SPS (20 mM in water; pH=5.0) resulted in the growth of multilayered RNase A-$R_9$/SPS films.

Figure 2:
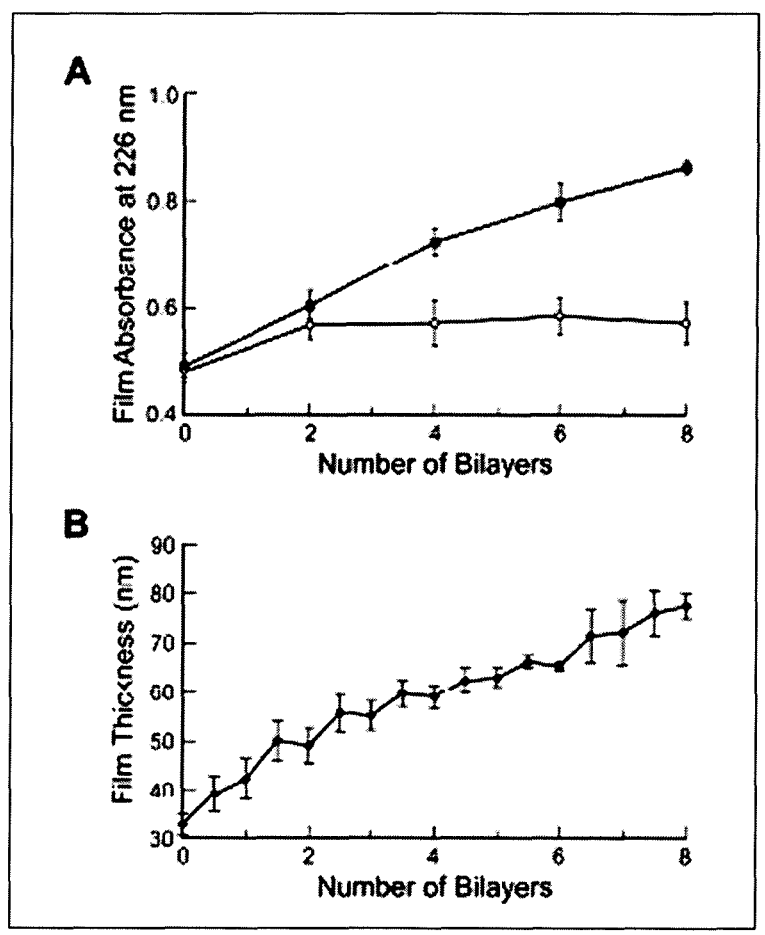
FIG. 2 shows graphs illustrating: A, film absorbance as a function of the number of bilayers; B, optical film thickness as a function of the number of bilayers.

FIG. 2A is a plot of absorbance (at 226 nm) versus the number of protein/SPS bilayers deposited onto quartz substrates. Data shown are for films fabricated using unmodified RNase A (○) or RNase A-$R_9$ (■). FIG. 2B is a plot of ellipsometric film thickness versus the number of RNase A-$R_9$/SPS bilayers deposited onto a silicon substrate. In both cases, substrates were precoated with 10 bilayers of an LPEI/SPS film prior to fabrication of the protein/SPS films.

FIG. 2A shows the increase in UV absorbance (at 226 nm, the absorbance maximum of SPS) for a representative RNase A-$R_9$/SPS film as a function of the number of protein/SPS layer pairs (referred to hereafter as "bilayers") deposited. These data demonstrate that film growth occurred in a linear manner, consistent with the growth of multilayered films fabricated from other conventional proteins. This linear growth profile provides convenient and predictable control over the amount of RNase A-$R_9$ immobilized at the surface of a coated substrate by control over the number of RNase A-$R_9$/SPS bilayers deposited. In contrast to films fabricated using RNase A-$R_9$, there was no significant film growth when solutions of RNase A not tagged with $R_9$ were used for film fabrication (at concentrations and pH values identical to those used above). As shown in FIG. 2A, the absorbance of substrates used to fabricate films using RNase A not tagged with $R_9$ remained essentially constant after the deposition of the first two bilayers.

RNase A-$R_9$/SPS and RNase A/SPS films were also fabricated on silicon substrates to characterize film growth and thickness using ellipsometry. As shown in FIG. 2B, films fabricated using RNase A-$R_9$ increased in optical thickness to yield films up to 80 nm thick after the deposition of eight bilayers. Although the overall growth profile for these films is linear, closer inspection of these data reveals that the majority of the increase in the thicknesses of these films resulted from the deposition of the protein-containing layers. On the basis of these ellipsometry data, the average thickness of each protein/SPS layer in these materials was calculated to be approximately 5.5 nm/bilayer.

In contrast to films fabricated using RNase A-R9, the optical thicknesses of films fabricated using solutions of RNase A that was not tagged with $R_9$ did not increase significantly for up to eight deposition cycles under otherwise identical fabrication conditions. These differences in film growth profiles are consistent with the large differences in film growth observed by UV absorbance (FIG. 2A).

Taken together, these experiments demonstrate: (1) that RNase A conjugated to $R_9$ can be incorporated effectively into multilayered films using SPS as an anionic film component; and (2) that RNase A-$R_9$ can be incorporated into films under conditions (e.g., 7 µM in water; pH 5.0) for which film growth does not occur using RNase A not tagged with $R_9$. These data indicate that the conjugation of $R_9$ facilitates the growth of multilayered films under these conditions. Not attempting to be bound by the following mechanism, this presumably occurs by increasing the strength of the electrostatic interactions between the more cationic protein and the anionic SPS. Nonaarginine may thus be viewed as a cationic "anchor", the conjugation of which permits the assembly of films under conditions that are not suitable for the assembly of films using native, unmodified RNase A.

Fabrication of Films Using RNase A-R9 and Poly(Acrylic Acid), Poly(Methacrylic Acid), or Poly($\alpha$-Propylacrylic Acid)

Multilayered films were fabricated on planar quartz and silicon substrates to facilitate characterization of film growth and thickness by UV/vis absorbance and ellipsometry, respectively. For all experiments, substrates were precoated with a thin multilayered film composed of LPEI and SPS (approximately 30 nm thick, with a topmost layer of SPS) to provide a charged surface suitable for subsequent adsorption of RNase A-R9. In all experiments, RNase A-R9 conjugates were labeled with fluorescein at residue 19 to facilitate the visualization and tracking of RNase A in subsequent cellular internalization studies described below (see also Fuchs and Raines, 2005).

In this example, fabrication of multilayered films was performed using an alternate dipping procedure. The iterative dipping of quartz or silicon substrates into RNase A-R9 (7.0 µM in water; pH=5) and PAA, PMAA, or PPAA (1 mg/mL in water; heated at 60° C.) resulted in the growth of multilayered RNase A-R9/(PAA, PMAA, or PPAA) films.

Figure 6:
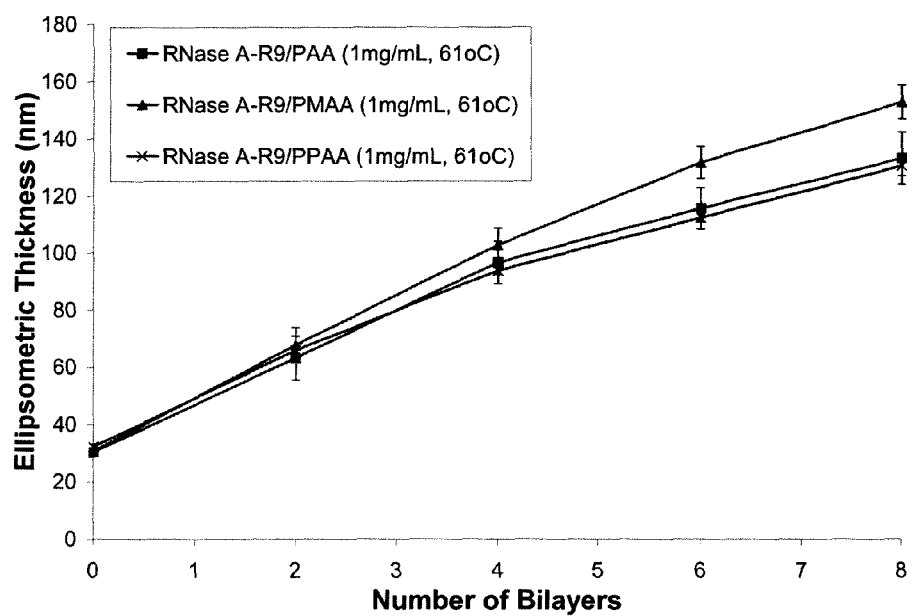
FIG. 6 shows a plot illustrating film thickness as a function of the number of bilayers for RNase A-R9/(PAA, PMAA, or PPAA) films.

FIG. 6 is a plot of ellipsometric film thickness versus the number of RNase A-R9/(PAA, PMAA, or PPAA) bilayers deposited onto a silicon substrate. These substrates were pre-coated with 10 bilayers of an LPEI/SPS film prior to fabrication of the protein/(PAA, PMAA, or PPAA) films. FIG. 6 shows a linear increase in ellipsometric thickness for representative RNase A-R9/(PAA, PMAA, or PPAA) films as a function of the number of protein/(PAA, PMAA, or PPAA) layer pairs (referred to as "bilayers") deposited. These data indicate that film growth occurred in a linear manner up to an optical thickness up to 150 nm thick, consistent with the growth of multilayered films fabricated from other conventional proteins. This linear growth profile provides convenient and predictable control over the amount of RNase A-R9 immobilized at the surface of a coated substrate by control over the number of RNase A-R9/(PAA, PMAA, or PPAA) bilayers deposited.

Incubation of RNase A/SPS Films and Release of RNase A

The stability of protein-containing films in aqueous environments has been investigated, with a view toward designing assemblies with properties tailored for specific applications. For example, films and assemblies that are stable in aqueous environments have been used to design catalytically-active membranes and microcapsules. In contrast, films and assemblies that are unstable or that erode in physiologically relevant media could be useful for the controlled, sustained, or localized release of proteins. Thus, multilayered polyelectrolyte assemblies can be disrupted, dissolved, or eroded upon changes in environmental pH, ionic strength, or other factors that change the nature of physical interactions in ionically-crosslinked materials. The inventors examined the stability of RNase A-R$_9$/SPS films in physiologically relevant media and determined that it was possible to use these materials for the sustained or localized delivery of RNase A from surfaces.

Quartz substrates coated with films fabricated using SPS and either RNase A-R$_9$ or unmodified RNase A were incubated in phosphate-buffered saline (PBS, pH 7.4, 137 mM NaCl) at 37° C. in UV-transparent cuvettes. Substrates were removed at predetermined intervals and the fluorescence of the incubation buffer was recorded directly from 514-520 nm (i.e., the maximum fluorescence emission range of fluorescein) and used to calculate the amount of protein released.

Figure 3:
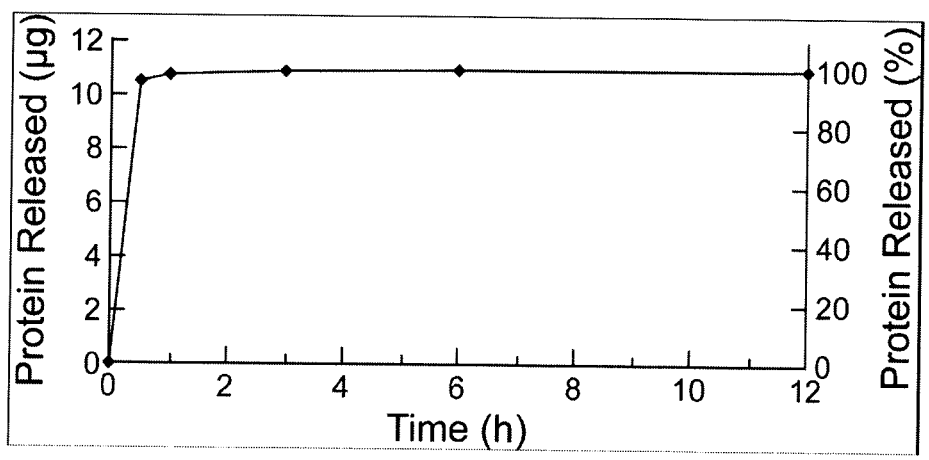
FIG. 3 is a graph illustrating the amount of protein released over time for an eight bilayer RNase A-R$_9$/SPS film incubated in PBS buffer at 37° C.

FIG. 3 shows a plot of the amount of protein released versus time for films fabricated from eight bilayers of RNase A-R$_9$/SPS. Inspection of these data reveals a rapid and large increase in protein release over the first 30 minutes (corresponding to approximately 96% of the protein released) and that the cumulative amount of protein released over this 12 hour period was about 11 µg. On the basis of these data and the dimensions of the film-coated portions of the substrates used in these experiments, RNase A-R$_9$/SPS films eight bilayers thick contained approximately 6.1 µg of RNase A-R$_9$ per cm$^2$. No significant increase in solution fluorescence was observed during the incubation of films fabricated using RNase A not modified with R$_9$, consistent with observations that unmodified RNase A is not incorporated effectively into multilayered assemblies under the conditions used herein (e.g., FIG. 2). The results in FIG. 3 indicate that films fabricated from SPS and RNase A-R$_9$ dissolve and release RNase A-R$_9$ into solution rapidly when incubated in PBS. Characterization of the thicknesses of RNase A-R$_9$/SPS films fabricated on silicon substrates using ellipsometry revealed large and rapid decreases in optical thickness from about 80 nm to about 35 nm after incubation in PBS for 30 min. This remaining thickness of 35 nm corresponds closely to the thickness of the LPEI/SPS foundation layers used to coat these silicon substrates prior to fabrication of the protein/SPS films. These ellipsometry data are thus consistent with the large and rapid increase in solution fluorescence shown in FIG. 3 over the same time period and provide additional support for the view that these films dissolve or disintegrate rapidly upon incubation in PBS.

It is possible to disrupt multilayered polyelectrolyte assemblies by changing environmental parameters such as pH or ionic strength that change the nature of the ionic interactions in these ionically crosslinked assemblies. The RNase A-R$_9$/SPS films used herein were fabricated using protein and polymer solutions prepared in water, but the release and stability experiments were conducted in phosphate buffered saline. Thus, while the cationic oligopeptide R$_9$ does facilitate film assembly in water, the electrostatic interactions in these assemblies may be effectively disrupted upon transfer to a medium of higher ionic strength.

The thickness of an RNase A-R$_9$/SPS film incubated in water (as opposed to PBS) did not decrease significantly for up to 200 h when incubated at 37° C. In combination with the results shown in FIG. 3, this control experiment provided support for the view that the large changes in pH and ionic strength that are experienced upon transfer to PBS play a significant role in the rapid dissolution and release of RNase A-R$_9$ from these materials. Objects coated with these materials can be used to exert spatial control over the release of protein and the internalization of protein by cells.

Incubation of RNase A/(PAA, PMAA, or PPAA) Films and Release of RNase A

Films and assemblies that are stable in aqueous environments have been used to design catalytically-active membranes and microcapsules. In contrast, films and assemblies that are unstable or that erode in physiologically relevant media can be useful for the controlled, sustained, or localized release of proteins. Several groups have reported that multi-layered polyelectrolyte assemblies can be disrupted or eroded upon changes in environmental pH, ionic strength, or other factors that change the nature of physical interactions in these ionically-crosslinked materials. The stability of RNase A-R$_9$/(PAA, PMAA, or PPAA) films in physiologically relevant media was determined, to establish that it is possible to use these materials for the sustained or localized delivery of RNase A from surfaces.

Silicon substrates coated with films fabricated using PAA, PMAA, or PPAA and RNase A-R$_9$ were incubated in phosphate-buffered saline (PBS, pH 7.4, 137 mM NaCl) at 37° C. in UV-transparent cuvettes. Substrates were removed at predetermined intervals and the fluorescence of the incubation buffer was recorded directly from 514-520 nm (i.e., the maximum fluorescence emission range of fluorescein). FIG. 7 shows a plot of percent protein released versus time for films fabricated from eight bilayers of RNase A-R$_9$/(SPS, PAA, PMAA, or PPAA). Inspection of these data reveals significant differences in the behavior. Whereas approximately 90-95% of protein was released from the RNase A-R9/(SPS, PAA, and PMAA) films within the first 20 h of incubation, only 60% of the protein was released from the RNase A-R9/PPAA film during the same incubation period. Further inspection of this profile revealed that protein was released from the RNase A-R9/PPAA film for up to 300 h.

Surface-Mediated Delivery of RNase A-R9 to Cells

The conjugation of protein transduction domains such as R$_9$ to proteins increases dramatically their transport into cells. The inventors established that ultrathin multilayered RNase A-R9/SPS films can be used to promote the surface-mediated delivery of RNase A to cells, i.e. protein transduction.

RNase A-R$_9$/SPS films composed of eight bilayers on planar quartz substrates were fabricated. Quartz substrates were used in these experiments to permit characterization of film growth using UV/vis spectrophotometry (e.g., FIG. 2A) and to permit the tracking of fluorescently-labeled RNase A-R$_9$ conjugates in cells using fluorescence microscopy. Film-coated slides were placed in direct contact with COS-7 cells growing in a reduced serum cell-culture medium (e.g., FIG. 4) and incubated in the presence of cells for 3 h. Cells were subsequently treated with fluorescent membrane and nuclear stains (WGA-Alexa 594 and Hoechst 34580) and imaged using LSCM without removal of the quartz slides.

Figure 4:
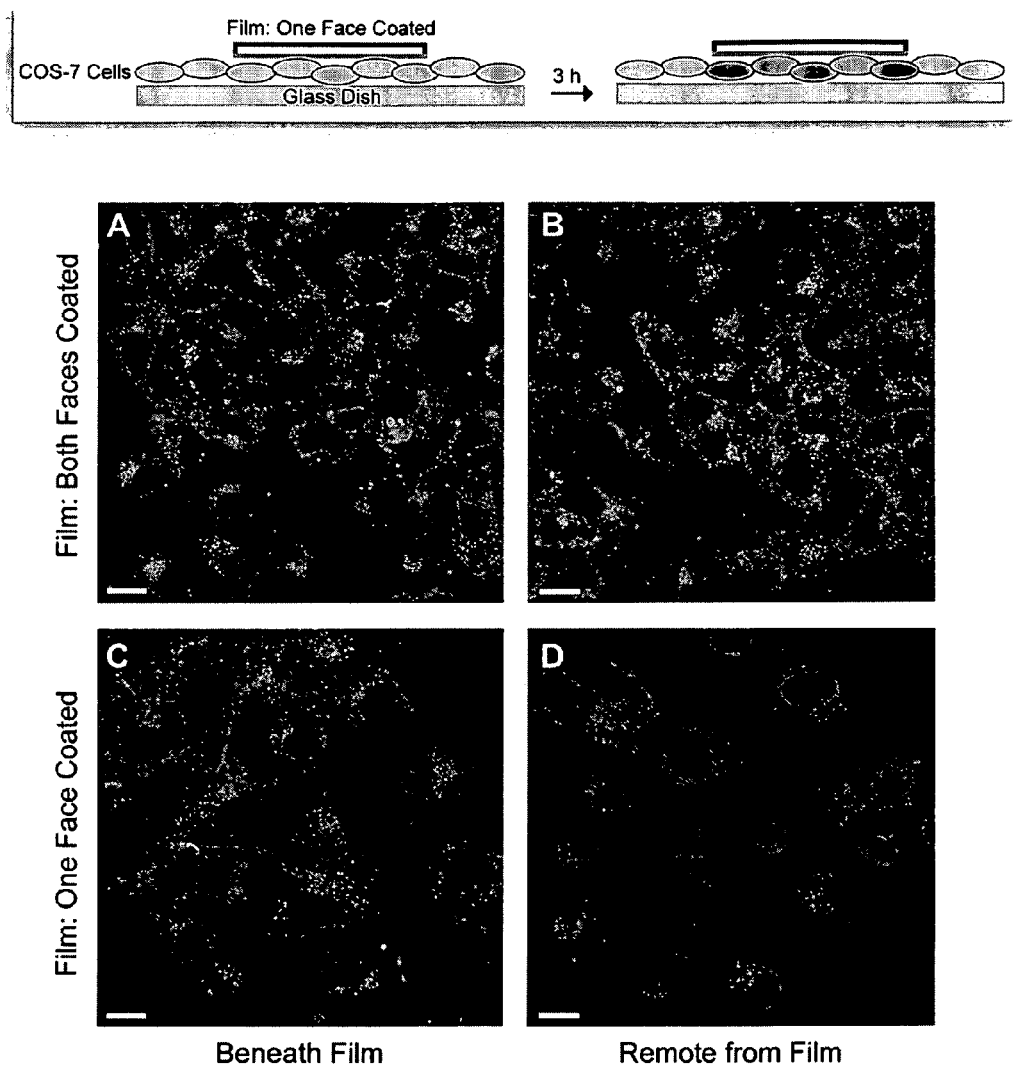
FIG. 4 shows: Top) General scheme illustrating surface-mediated protein transduction in cells promoted by placing film-coated quartz slides in contact with cells; Bottom) LSCM images of COS-7 cells incubated in the presence of film-coated quartz slides.
Figure 5:
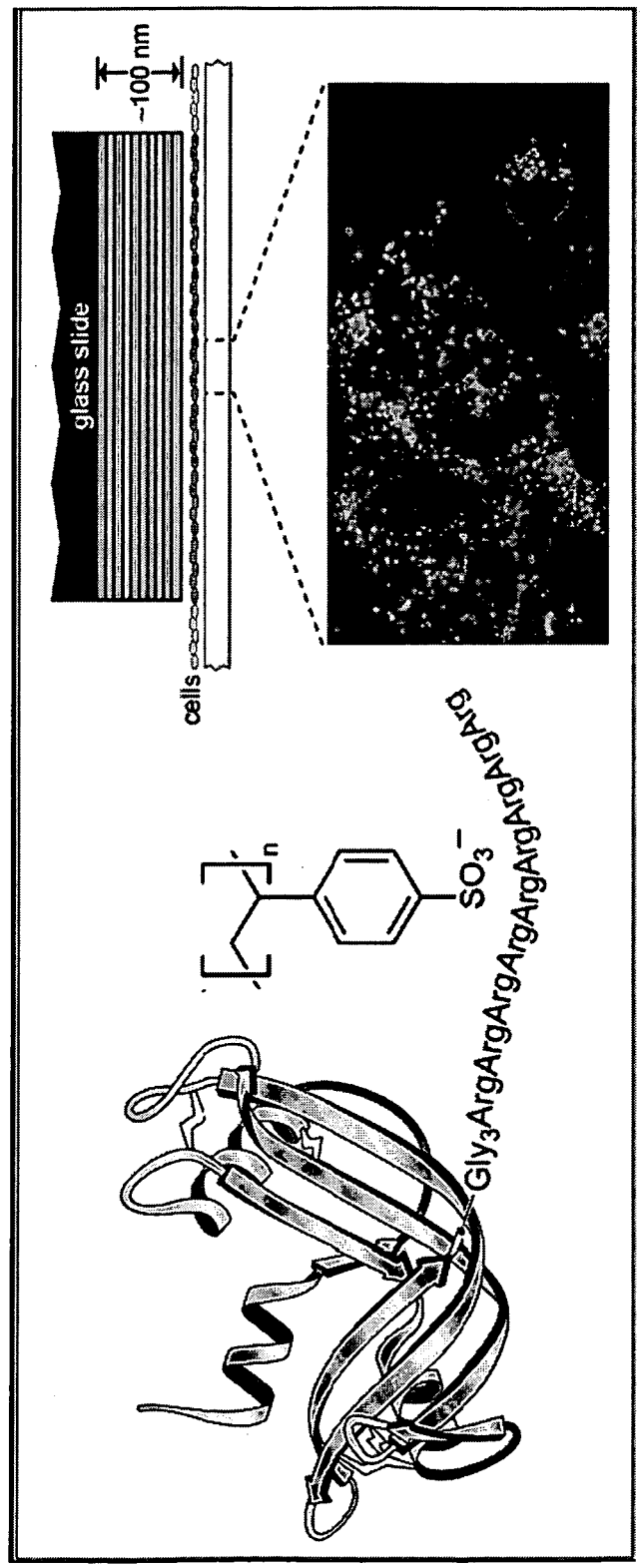
FIG. 5 is a schematic illustration of one example of a composition and method of this invention.

FIG. 4, Top, is a general scheme illustrating surface mediated protein transduction in cells promoted by placing film-coated quartz slides in contact with cells. FIG. 4, Bottom, shows LSCM images of COS-7 cells incubated in the presence of film-coated quartz slides. FIG. 4A) shows cells growing directly beneath a slide coated on both faces. FIG. 4B) shows cells growing in a remote location in the culture well not in direct contact with the slide in panel A. FIG. 4C) shows cells growing directly beneath a slide coated on a single face. FIG. 4D) shows cells growing in a remote location in the culture well not in direct contact with the slide in panel C. The red, green, and blue channels in FIG. 4A-D, as shown in U.S. Provisional Patent Application Ser. No. 60/881,788, and in Jewell et al., 2007, *Biomacromolecules* 8: 857-863, both of which are incorporated herein by reference, correspond to WGA-Alexa 594, fluorescein, and Hoechst fluorescent probes, respectively. Scale bar=20 μm.

FIGS. 4A and 4B show representative 60×, three-color LSCM images of COS-7 cells incubated in the presence of a quartz slide coated with RNase A-R$_9$/SPS films on both sides (i.e., on both the top and bottom faces of the slide). These images demonstrate that RNase A-R$_9$ is internalized efficiently by cells, as was determined by the presence of numerous punctate green fluorescent spots in nearly all cells. The observation of punctate fluorescence is consistent with the inventors' previous observations that proteins and peptides conjugated to R$_9$ are trafficked to, and largely sequestered in, endosomes and lysosomes after internalization by cells (Fuchs and Raines, 2005, *Protein Sci.* 14: 1538-1544; Fuchs and Raines, 2004, *Biochemistry* 43: 2438-2444). While FIG. 4A demonstrates the internalization of protein in cells growing directly beneath the film-coated slide, high levels of transduction were also observed in cells that were located in remote locations of the culture well (FIG. 4B). This non-localized protein transduction likely resulted from the release of RNase A-R$_9$ from the top face of the coated slide (i.e., the face not placed in contact with cells), followed by the internalization of soluble protein by cells in adjacent areas of the culture well. These results are consistent with the results of the inventors' past studies using DNA-containing films, in which significant levels of non-localized cell transfection were observed when quartz slides coated on both sides were placed in direct contact with cells (Jewell et al., 2005, *J. Control. Release* 106: 214-223).

Quartz slides were also coated on only a single face by obscuring one side of a slide with commercially available rubber cement prior to film fabrication. Removal of the rubber cement after film deposition resulted in quartz slides coated with an RNase A-R$_9$/SPS film on only one side. Slides prepared in this manner contained about 50% of the RNase A-R$_9$ immobilized on slides coated on both sides, as determined by UV/vis spectrophotometry. When these slides were placed face down on cells, protein transduction was localized largely to cells growing directly beneath the films rather than cells growing in adjacent areas of the culture well (e.g., FIG. 4C versus 4D).

The results above demonstrate that films fabricated from RNase A-R$_9$ and SPS dissolve rapidly when incubated in physiologically relevant environments and that macroscopic objects coated with these materials can be used to promote the surface-mediated delivery of RNase A-R$_9$ to cells. However, several additional important points deserve comment. First, past studies have demonstrated that proteins can be incorporated into multilayered films without changes in protein structure or loss of biological function. Fluorescence-based enzyme activity assays were conducted using aliquots of PBS containing RNase A-R$_9$ released from RNase A-R$_9$/SPS films. These experiments demonstrated that a substantial fraction of the RNase A released from these materials remained catalytically active. However, several synthetic polyanions are known to be potent inhibitors of RNase A. These experiments suggest that the presence of SPS in these solutions can act to inhibit the activity of RNase A in these assays, and thus additional analytical experiments can be conducted to establish quantitatively the activity of the RNase A released from these materials. Second, although the RNase A-R$_9$/SPS films investigated here dissolve and release their contents rapidly, it may prove possible to incorporate new polymer structures or other design elements that permit gradual erosion and the sustained release of protein. Finally, many past studies have demonstrated the conjugation of cationic protein transduction domains to proteins of therapeutic and biotechnological interest. The present invention thus suggests the basis of methods that could be used to fabricate ultrathin films that permit the localized delivery of therapeutic proteins to cells and tissues.

In one embodiment, the present invention provides a general approach for the incorporation of proteins into multilayered polyelectrolyte assemblies that makes use of cationic protein transduction domains. Conjugation of the cationic protein transduction domain nonoarginine (R$_9$) to RNase A results in an increase in positive charge and, as a result, an increase in the extent to which RNase A is internalized by cells. The conjugation of R$_9$ to RNase A permits the incorporation of RNase A into films under conditions that do not allow for incorporation of the unmodified protein. This result suggests that R$_9$ functions as a cationic "anchor" that increases the strength of electrostatic interactions with SPS and facilitates layer-by-layer assembly. In addition, films fabricated from RNase A-R$_9$ and SPS dissolve and release RNase A-R$_9$ into solution rapidly when incubated in physiologically relevant environments. These materials can thus be used to localize the release of RNase A-R$_9$ and the internalization of this protein by cells. The placement of film-coated quartz slides in contact with COS-7 cells resulted in high levels of protein transduction in cells that were growing under or in contact with these materials. Many past studies have demonstrated the feasibility of conjugating R$_9$ or other synthetic or naturally occurring cationic protein transduction domains to proteins of therapeutic and biotechnological interest. The present invention thus provides for the design of ultrathin films and coatings that permit the localized delivery of therapeutic proteins from the surfaces of implantable materials and/or provide spatial and temporal control over the release and internalization of engineered proteins in other biotechnological applications.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered and obvious to those skilled in the art of molecular biology, biotechnology, nanotechnology and nanobiology, are within the scope of this invention. All publications, patents, and patent applications cited herein are incorporated by reference in their entirety for all purposes.

What is claimed is:

1. A multilayered film comprising a bilayer capable of dissolving in physiological media, said bilayer comprising:
    a) a negatively charged polyelectrolyte layer consisting essentially of an anionic polymer; and
    b) a second layer comprising a positively charged molecule conjugated to a charged small molecule transduction domain, wherein the charged small molecule transduction domain is a cationic protein transduction domain,
    wherein the positively charged small molecule transduction domain-conjugated molecule within the bilayer electrostatically interacts with the negatively charged anionic polymer and is released from the multilayer film when the bilayer dissolves.

2. The multilayered film of claim 1 wherein the cationic protein transduction domain comprises a cationic oligoaminoacid tail.

3. The multilayered film of claim 1 wherein the cationic protein transduction domain comprises a cationic oligoaminoacid tail comprising between 2 and about 30 residues.

4. The multilayered film of claim 1 wherein the cationic protein transduction domain comprises polyarginine.

5. The multilayered film of claim 4 wherein the polyarginine is nonaarginine.

6. The multilayered film of claim 1 further comprising a molecular linker conjugated to the charged small molecule transduction domain.

7. The multilayered film of claim 1 wherein the anionic polymer is sodium polystyrene sulfonate.

8. The multilayered film of claim 1 wherein the anionic polymer is selected from the group consisting of sodium poly(styrene sulfonate), poly(acrylic) acid, poly(methacrylic) acid, and poly(a-propylacrylic acid).

9. The multilayered film of claim 1 wherein the positively charged molecule is a positively charged peptide or a protein.

10. The multilayered film of claim 9 wherein the positively charged molecule is RNase A.

11. The multilayered film of claim 1 wherein the multilayered film comprises eight or more bilayers wherein each bilayer comprises:
    a) a negatively charged polyelectrolyte layer consisting essentially of an anionic polymer; and
    b) a second layer comprising a positively charged molecule conjugated to a charged small molecule transduction domain, wherein the charged small molecule transduction domain is a cationic protein transduction domain,
    wherein the anionic polymer in one bilayer can be the same or different as the anionic polymer in another bilayer, and the positively charged small molecule transduction domain-conjugated molecule in one bilayer can be the same or different as the positively charged small molecule transduction domain-conjugated molecule in another bilayer, and
    wherein the positively charged small molecule transduction domain-conjugated molecule within each bilayer electrostatically interacts with the negatively charged anionic polymer within that bilayer and is released from the multilayer film when the bilayer dissolves.

12. A method for fabrication of a multilayered assembly, the method comprising:
    providing a substrate,
    depositing one or more bilayers capable of dissolving in physiological media on said substrate, wherein depositing one or more bilayers comprises:
    a) depositing a negatively charged polyelectrolyte layer free of charged small molecule transduction domain, wherein said polyelectrolyte layer consists essentially of an anionic polymer, and
    b) depositing a second layer in contact with the negatively charged polyelectrolyte layer, said second layer comprising a charged small molecule transduction domain conjugated to a positively charged molecule, wherein the charged small molecule transduction domain is a cationic protein transduction domain,
    wherein the positively charged small molecule transduction domain-conjugated molecule electrostatically interacts with the negatively charged anionic polymer and is released from the multilayer film when the bilayer dissolves.

13. A method, comprising contacting the multilayered film of claim 1 with a cell for a time sufficient to allow the molecule to enter the cell.

14. A method for delivery of a small molecule into a cell, the method comprising:
    a) providing a composition comprising: a multilayered film comprising a bilayer capable of dissolving in physiological media, said bilayer comprising:
        i) a negatively charged polyelectrolyte layer consisting essentially of an anionic polymer; and
        ii) a second layer comprising a positively charged molecule conjugated to a charged small molecule transduction domain, wherein the charged small molecule transduction domain is a cationic protein transduction domain,
        wherein the positively charged small molecule transduction domain-conjugated molecule within the bilayer electrostatically interacts with the negatively charged anionic polymer and is released from the multilayer film when the bilayer dissolves; and
    b) contacting the composition with the cell for a time sufficient to allow the small molecule to enter the cell.

15. The method of claim 14 wherein the cationic protein transduction domain comprises polyarginine.

16. The method of claim 15 wherein the polyarginine is nonaarginine.

17. The method of claim 14 wherein the anionic polymer is selected from the group consisting of sodium poly(styrene sulfonate), poly(acrylic) acid, poly(methacrylic) acid, and poly(a-propylacrylic acid).

* * * * *